United States Patent
El-Andaloussi et al.

(10) Patent No.: US 9,441,246 B2
(45) Date of Patent: Sep. 13, 2016

(54) ADENO-PARVOVIRUS CHIMERA WITH ENHANCED ONCOLYTICAL POTENTIAL

(71) Applicant: DEUTSCHES KREBSFORSCHUNGSZENTRUM, Heidelberg (DE)

(72) Inventors: Nazim El-Andaloussi, Heidelberg (DE); Antonio Marchini, Heidelberg (DE); Jean Rommelaere, Heidelberg (DE)

(73) Assignee: DEUTSCHES KREBSFORSCHUNGSZENTRUM, Heidelberg (DE)

( * ) Notice: Subject to any disclaimer, the term of this patent is extended or adjusted under 35 U.S.C. 154(b) by 84 days.

(21) Appl. No.: 14/148,114

(22) Filed: Jan. 6, 2014

(65) Prior Publication Data
US 2014/0235699 A1 Aug. 21, 2014

Related U.S. Application Data

(63) Continuation-in-part of application No. PCT/EP2012/002860, filed on Jul. 6, 2012.

(30) Foreign Application Priority Data

Jul. 7, 2011 (EP) .................................. 11005568

(51) Int. Cl.
C12N 7/00 (2006.01)
C12N 15/86 (2006.01)

(52) U.S. Cl.
CPC .............. *C12N 15/86* (2013.01); *C12N 7/00* (2013.01); *C12N 2710/10331* (2013.01); *C12N 2710/10344* (2013.01); *C12N 2750/14332* (2013.01); *C12N 2750/14351* (2013.01); *C12N 2799/02* (2013.01); *C12N 2830/006* (2013.01)

(58) Field of Classification Search
None
See application file for complete search history.

(56) References Cited

FOREIGN PATENT DOCUMENTS

WO 03/061582 A2 7/2003

OTHER PUBLICATIONS

Raykov et al. Transient suppression of transgene expression by means of antisense oligonucleotides: a method for the production of toxin-transducing recombinant viruses. Gene Therapy, 2002; 9: 358-362.*
Maxwell and Maxwell. Control of parvovirus DNA replication by a tetracycline-regulated repressor. Gene Therapy, 1999; 6: 309-313.*
Marchini and Rommelaere. Targeting of the oncolytic parvovirus to HPV positive cells using an adenovirus-H-1PV hybrid vector: restoring death pathways in tumor cells. Deutsches Krebsforschungszentrum (DKFZ)/Canceropole Grand-Est {CGE} Joint research programme in Applied Tumour Virology. 2006: 1-7.*
International Search Report corresponding to PCT/EP2012/002860 mailed Jan. 23, 2013.

(Continued)

*Primary Examiner* — Janet L Andres
*Assistant Examiner* — Stuart W Snyder
(74) *Attorney, Agent, or Firm* — Vedder Price P.C.; Thomas J. Kowalski; Deborah L. Lu

(57) ABSTRACT

Described is a chimerical adenovirus-parvovirus vector characterized in that it comprises the entire parvovirus genome inserted into a adenovirus genome, wherein: (a) the adenovirus genome is characterized by deletion of E1 and E3, and (b) the biological activity of the parvoviral protein NS, preferably NS1, is reduced or eliminated.

19 Claims, 32 Drawing Sheets

(56) References Cited

OTHER PUBLICATIONS

Maxwell, IH, et al., "Control of parovirus DNA replacation by a tetracycline-regulated repressor," Gene Therapy (1999), pp. 309-313.

El-Andaloussi, N., et al., "Novel adenovirus-based helper system to support production of recombinant parvovirus," Cancer GeneTherapy (2011) 18, pp. 240-249.

El-Andaloussi, N., et al., "Generation of an Adenovirus-Parvovirus Chimera with Enhanced Oncolytic Potential," Journal of Virology, vol. 86, No. 19, Jul. 11, 2012, pp. 10418-10431.

Raykov, Z., et al., "Transient suppression of transgene expression by means of antisense oligonucleotides: a method for the production of toxin-transducing recombinant viruses," Gene Therapy (2002) 9, pp. 358-362.

Marchini, A., et al., "Research project proposal: Targeting of the oncolyic parvovirus to HPV positive cells using an adenovirus-H-1PV hybrid vector: restoring death pathways in tumor cells," 2006, pp. 1-7, XP002664653.

Lagrange, M., et al., "Modification of adenovirus type 5 tropism for a preferential transduction of human papillomavirus-positive cancer cells," Arch Virol (2008) 153:1921-1925.

English Translation of Japanese Office Action dated Mar. 26, 2015, which issued during prosecution of Japanese Application No. 2014-517524.

Fussenegger, M. et al. "The impact of mammalian gene regulation concepts on functional genomic research, metabolic engineering, and advanced gene therapies" Biotechnol. Prog., 17(1)1-51. 2001.

Kuate, Seraphin, et al. "Production of lentiviral vectors by transient expression of minimal packaging genes from recombinant adenoviruses" The Journal of Gene Medicine 6(11):1197-1205, 2004.

Lagrange, M. et al. "Modification of adenovirus type 5 tropism for a preferential transduction of human papillomavirus-positive cancer cells" Arch. Virol. 153(10):1921-1925, 2008.

\* cited by examiner

A

B

A

B

A HeLa

Infection

B CxCa

Infection 48h p.i.

72h p.i.

A

B

A

B

ADENO-PARVOVIRUS CHIMERA WITH ENHANCED ONCOLYTICAL POTENTIAL

RELATED APPLICATIONS AND INCORPORATION BY REFERENCE

This application is a continuation-in-part application of international patent application Serial No. PCT/EP2012/002860 filed 6 Jul. 2012, which published as PCT Publication No. WO 2013/004396 on 10 Jan. 2013, which claims benefit of European patent application Serial No. 11005568.8 filed 7 Jul. 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a chimeric adeno-parvovirus vector characterized in that it may comprise the entire parvovirus genome inserted into an adenovirus genome, wherein: (a) the adenovirus genome is characterized by deletion of E1 and E3, and (b) the biological activity of at least a parvoviral protein NS, in particular NS1, is (preferably: transiently) repressed or even blocked during the chimera production process but is fully functional in cancer cells.

BACKGROUND OF THE INVENTION

Novel targeted approaches for the treatment of various cancer types are urgently needed. Oncolytic viruses hold promise for the treatment of cancers, because they can target cancer cells without harming normal cells. Among them, two groups of viruses attract much attention as alternative antineoplastic agents: the adenoviruses and the autonomous parvoviruses. Adenoviruses (Ad) have been engineered to function as vectors for delivering therapeutic genes for gene therapy, and as direct cytotoxic agents for oncolytic viral therapy. Rodent autonomous parvoviruses (PVs), on the other hand, show oncolytic and oncosupressive properties and are non-pathogenic for humans.

Adenoviruses (Ads) are non-enveloped, icosahedral, double-stranded DNA viruses. As of today, over 50 different human serotypes have been described with most of them infecting the respiratory or gastrointestinal tracts and the eye [1]. Ad infections are very common and generally not associated with any serious pathogenicity. The Ad genome comprises 30-38 kbp, and is delivered to the nucleus of infected host cells. Ads represent the most popular gene therapy vectors, and were used in about 25% of approved phases I to III clinical trials for vaccine and therapeutic gene transfer during the last 2 decades [2, 3]. This is largely due to the ability of these vectors to efficiently deliver trangenes to a wide range of different cell types [1]. Furthermore, Ads are very versatile tools with remarkable DNA packaging capacity, offering a plethora of possibilities for genetic manipulations. The Ad genome can be modified in different ways in order to restrict its replication or expression to specific tumour cells [4]. Furthermore, it is possible to re-direct Ad entry and render it more specific for cancer cells, through the use of molecular adaptors or genetic engineering of Ad capsid [5, 6]. In addition, Ads can be produced at high titers and quality under good manufacturing practice conditions [6]. As a result, ONYX-015, a hybrid of virus serotype Ad2 and Ad5 with deletions in the E1B-55K and E3B regions was the first engineered replication-selective virus to be used in clinical trials against various tumour entities and a modification of this vector, the E1B-55K deleted adenovirus H101, received marketing approval in China in 2005 for the treatment of head and neck cancer [7, 8].

Autonomous rodent parvoviruses (PVs) are small icosahedral, non-enveloped single-stranded DNA viruses. Their genome is about 5.1 kb long and contains two promoters, P4 and P38, that control the expression of the non-structural (NS1 and NS2) and structural (VP1 and VP2) proteins, respectively [9]. Several PVs, including the minute virus of mice (MVM) and the rat H-1PV, have been shown to be oncolytic and oncosuppressive in various cellular and animal cancer models [10]. Additionally, PVs are non-pathogenic and show low prevalence in humans, favoring their use as therapeutics [11]. H-1PV will be evaluated shortly in a phase I/IIa clinical trial for the treatment of patients with recurrent glioblastoma multiforme [10]. The antineoplastic property of these PVs is due, at least in part, to preferential viral DNA replication and gene expression in malignant cells. This could be traced back to the dependence of parvoviruses on S-phase, and more particularly on cellular factors such as E2F, CREB, ATF and cyclin A which are known to be overexpressed in cancer cells [10]. In addition PVs may take also advantage of the common inability of malignant cells to mount an efficient anti-viral innate immune response [12]. It has been shown that PVs have the ability to induce cell cycle arrest [13] and different death pathways in cancer cells, including necrosis [14], apoptosis [13, 15] and lysosomal dependent cell death [16]. NS1 is the major effector of parvovirus oncotoxicity [13]. Although preclinical studies highlight the anticancer potential of PVs, this feature should be further reinforced in view of the clinical application of these agents. One major limitation lies in the fact that PVs bind and enter into a variety of normal human cells, resulting in the sequestration of a large portion of the administered viral dose away from the tumor target cells. Retargeting PV entry to tumor cells would thus increase the efficacy of PV-based treatments and provide additional safety against eventual side-effects on normal tissues. Furthermore, replication-competent PVs have a limited capacity for accommodating transgenes and tolerate only the insertion of a short transgene (300 bp maximum), thereby hampering strategies to reinforce the anticancer efficacy of PVs by arming them with therapeutic transgenes. It should be also stated that large scale production of PVs, as required for clinical applications, remains a major limitation.

The development of an Ad hybrid vector harboring only part of the parvovirus genome (a parvovirus gene expressing cassette including the P4-NS1-P38 region) and not the whole parvovirus genome has been previously described [36]. For instance, the hybrid described in [36] lacks the ITR regions including NS1-specific nicking sites which are essential for NS1-mediated excision and release of the PV genome from the adenovirus backbone in target cancer cells. It also misses the VP gene precluding the possibility to generate fully infectious parvovirus particles.

An Ad5 adenovirus comprising an AAV genome having the Rep genes controlled by a Tet dependent repressor has been previously described [37]. AAV are dependoviruses and although they belong to the Parvoviridae family they show remarkable differences compared to parvoviruses and are well distinguished viruses therefrom. Most importantly, AAVs depend on a helper virus such as Adenovirus for efficient replication while parvoviruses such as H-1PV are replication competent.

Thus, the problem on which the present invention is based was to provide a means (a) for increasing the efficiency of parvovirus production, (b) for increasing the specificity to cancer cells, and (c) for overcoming the current limitations regarding the insertion/expression of therapeutic transgenes that could complement and reinforce PV-antitumour activities.

This technical problem is solved by providing the embodiments characterized in the claims.

Since the early 1970s, DNA recombinant technology made it possible genetic engineering of a variety of viral vectors, in order to match their needs [17]. In particular, viral chimeras were generated both to analyze the parental viruses [18] and to obtain novel artificial virions that combined the desired properties of the parental viruses and compensate for some of their current limitations [18-25]. In the experiments resulting in the present invention an adeno-parvovirus (Ad-PV) chimera was created by inserting the complete genome of hH-1 PV into the Ad5 genome deleted of the E1 and E3 regions (Ad5ΔE1ΔE3) expecting that this chimera may enhance PV replication in cancer cells through the concomitant expression of Ad helper functions [26-28]. Longer-term benefits for PV-based cancer therapy may also include: (i) the specific delivery of PV genomes to cancer cells by means of retargeted Ads and (ii) Ad genome arming with therapeutic transgenes that potentiate the PV killing activity. Would an adenoviral vector endowed with oncolytic properties be used, the PV component of the chimera should reinforce this antineoplastic activity by (i) expressing the cytotoxic NS1 protein under its natural PV promoter, and (ii) amplifying the antitumour effect through PV excision from the vector, autonomous replication and spreading through the tumor.

The first attempts to develop Ad-PV chimeras failed at the production stage due to the strong negative interference of PV non-structural (NS) proteins, with hybrid vector replication. Thus, a strategy for tightly controlling the expression of the viral NS proteins during the chimera production process was devised. To this end, first the H-1PV-TO parvovirus was engineered, in which the early P4 promoter, controlling the expression of the NS gene unit, was modified by inserting tetracycline operator (TO) elements [29, 30]. In HEK T-REx™-293 cells, which constitutively express the Tet repressor (TetR), the activity of P4-TO was completely inhibited, and consequently neither expression of NS1 protein nor PV replication was detected unless the tetracycline analogous, doxycycline (dox) was added to the medium. On the contrary, in cancer target cells, which do not express TetR, the P4 was fully functional to wild-type levels. Based on these results, the PV-TO genome was inserted into the Ad DNA backbone, generating the Ad-PV-TO chimera. In keeping with above results, the blockage of NS expression, allowed the chimera to be produced at high titers in T-REx™-293 cells. The Ad-PV-TO chimera proved able to efficiently deliver its PV component to cancer cells in which the parvoviral genome was excised from the vector and replicated autonomously, yielding progeny PV particles. Most remarkably the Ad-PV-TO was more efficient in killing various cancer cell lines than the parental PV or Ad (used alone or in combination).

Citation or identification of any document in this application is not an admission that such document is available as prior art to the present invention.

SUMMARY OF THE INVENTION

This is the first demonstration that an infectious viral (PV) molecular clone can be loaded and delivered by a different viral vector (Ad), from which it gets rescued and autonomously amplifies in target cells. The Ad-PV chimera represents a potential launching platform for an innovative viral strategy against cancer that could combine all in one: cancer selective retargeting, viral oncolysis and cancer gene therapy.

In summary, the chimeras of the present invention are characterized by the following advantages in view of the PV of the prior art:

First, they connect two areas of research and development: Parvovirology and adenovirology. Parvoviruses could benefit from the advanced technologies developed in the adenovirus field. On the other hand, PV will enhance the antineoplastic activity of Ad by (i) expressing the cytotoxic NS1 protein under the strong PV P4 promoter, and (ii) by amplifying the antitumour effect by means of PV replication and spreading through the tumor.

Second, they have improved anticancer efficacy. Ad-PV is a stronger anti-cancer agent than its parental viruses against various cancer cell lines.

Third, they improve PV production. Ad-PV has the potential, like any Ad-based vectors, to be produced in large amounts under GMP conditions compatible with clinical needs. This could overcome the difficulties in producing PV and parvovirus based vectors.

Fourth, they improve PV cancer specificity. It is now possible to improve the cancer specificity of parvovirus taking advantage of the Ad-retargeting technologies. Indeed, cancer retargeted Ads (e.g. obtained by inserting into the Ad capsid cancer-specific peptides, ligands, adaptors, affibody molecules, single chain antibodies etc.) (7) could be used for the development of a second generation of Ad-PV chimeras that could be used as a vehicle for the specific delivery of parvovirus genome into cancer cells.

Fifth, they improve PV-antineoplastic efficacy and pave the way for the development of innovative anti cancer strategies. Ad-PV offers the capacity to accommodate into its genome other therapeutic transgenes (up to 5 kilobases). With further deletions into the Ad genome, the free space open for genetic manipulation could be expanded to 30 kilobases. Ad-PV could accommodate supplementary genetic PV boosters (e.g. molecules that could enhance PV oncolysis and/or PV replication in malignant cells) and/or a concomitant cancer gene therapy.

Sixth, they increase the possibilities of intervention. Ad-PV chimeric genome could be encapsidated within a panel of different immunological distinct Ad-capsids, allowing repeated Ad-PV administrations to the same patient, circumventing previous anti Ad-PV humoral response and increasing possibilities of intervention. In the same line, Ad-PV could be used to deliver PV genome to a patient that already received a PV treatment and that already developed anti-PV neutralizing antibodies.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE FIGURES

The following detailed description, given by way of example, but not intended to limit the invention solely to the specific embodiments described, may best be understood in conjunction with the accompanying drawings.

FIG. 12: DNA constructs. (A) pShuttle-hH-1-TO, (B) pAd-hH-1-TO.

DETAILED DESCRIPTION OF THE INVENTION

Figure 1:
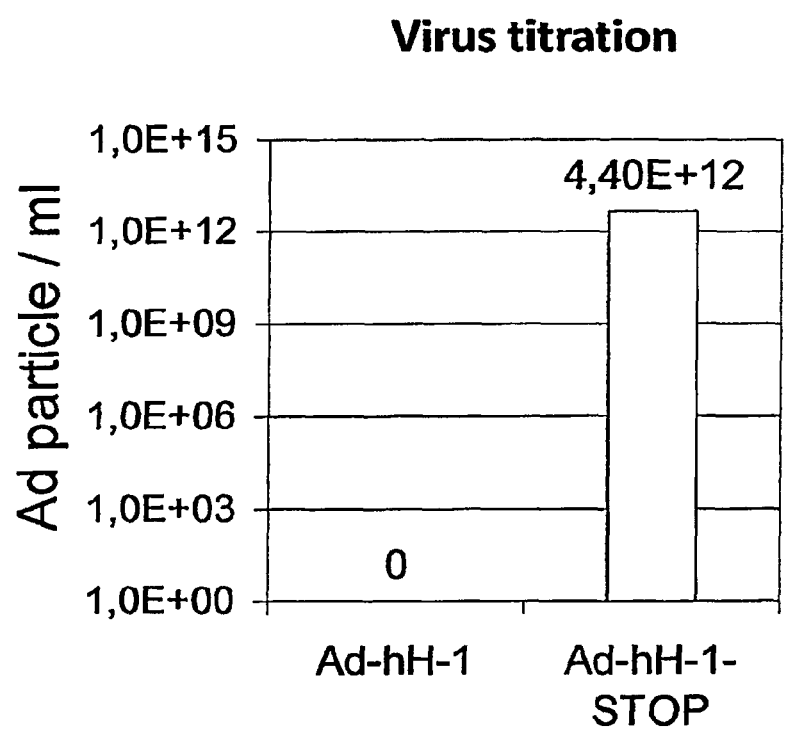
FIG. 1: Interference of Parvovirus non structural proteins with Adeno-Parvovirus chimera production. 293 cells were transfected with pAd-hH-1 or pAd-hH-1-STOP in which 3 STOP codons were inserted into the NS open reading frame. After one week, cells were lysed and their crude extracts were inoculated to fresh 293 cells for a second round of virus amplification through infection. Cell lysates from these cultures were purified twice by CsCl ultracentrifugation and the adenoviruses particles produced were measured through their absorbance at 260 nm.

Thus, in a first aspect the present invention relates to a chimeric adeno-parvovirus vector characterized in that it comprises the entire parvovirus genome inserted into an adenovirus genome, wherein:
(a) the adenovirus genome is characterized by deletion of E1 and E3; and
(b) the biological functions of at least one NS protein, in particular NS1, are (preferably: transiently) repressed or blocked in the packaging cell line during the chimera production but are fully functional in cancer cells.

The person skilled in the art can arrive at adenovirus nucleotide sequences having a deletion of E1 and E3 starting from the known nucleotide sequences of adenovirus using methods known in the art. The reduction or elimination of the biological activity of at least one or more parvoviral protein NS (preferably NS1 and/or NS2) can be achieved by several ways known to the person skilled in the art, e.g., by modifying the amino acid sequence of the protein resulting in inactive and/or truncated versions of the protein or, preferably, by reducing or eliminating the expression of the gene encoding said protein(s), e.g., by modifying the parvoviral P4 early promoter directing the expression of NS. Preferably, the promoter is modified in such way that expression can be selectively suppressed during propagation of the chimeric virus for production in high amounts but is restored for therapeutic application of the chimeric vector/virus to the patient, i.e., in the cancer cells of the patient NS is expressed. Preferably, the P4 early promoter is modified in such a way that expression can be transiently blocked by a tetracycline repressor as described in the examples, below. In cancer cells which do not express the TetR, the P4 promoter is fully functional.

Preferably, the adenovirus genome of the chimeric adeno-parvovirus vector of the invention is the genome of Ad5.

In the chimerical adenovirus-parvovirus vector of the invention the parvovirus is a rodent parvovirus. Preferred rodent parvoviruses are LuIII, Mouse minute virus (MMV), Mouse parvovirus (MPV), Rat minute virus (RMV), Rat parvovirus (RPV), Rat virus (RV) or H1 (H1-PV). Preferably, the parvovirus is derived from parvovirus H1.

In addition, the chimeric adeno-parvovirus vector of the invention may contain a gene coding for an expressible transgene, e.g., for a detectable phenotypic marker so as to prove the successful introduction into the target cell. Preferably, the marker protein is a fluorescent protein. This readily proves a transfection of the desired target cell. Examples of suitable genes coding for fluorescent proteins are rfp-(red), gfp-(green), cfp-(cyan) and yfp-(yellow) gene, rfp-(red) (Dsred-cDNA; Clontech) being preferred. In a further embodiment of the chimeric adeno-parvovirus vector of the invention the transgene is a gene encoding a therapeutic or immunogenic polypeptide which might support the therapeutic benefit of the vector of the invention. Examples of such transgenes are: a cytotoxic polypeptide, cytokine, chemokine, shRNAs, microRNAs, a cancer-specific peptide, ligand, adaptor, affibody, single chain antibody and/or a polypeptide enhancing PV oncolysis and/or PV replication.

Examples of suitable promoters for driving expression of the transgene, are RSV (rous sarcoma virus) promoter, CMV (cytomegalovirus) promoter, HSV (herpes simplex virus) tk promoters or the P38 promoter of the autonomous parvovirus minute virus of mice which is strongly transactivated by the nonstructural protein NS1, a sequence-specific DNA-binding protein. The P38 promoter is preferred. The expression cassette (promoter/e.g. marker gene/polyadenylation site) is inserted in the vector at a suitable site which can easily be determined by the person skilled in the art.

In a second aspect, the present invention relates to a method of preparing a chimeric adeno-parvovirus vector characterized in that
  (i) mammalian cells are transfected with a chimeric adeno-parvovirus vector of the invention and cultured under conditions blocking the expression of the parvoviral NS transcription unit; and
  (ii) the chimeric adeno-parvovirus is isolated from the mammalian cells or the medium after culturing the cells.

Thus, recombinant particles are produced by introducing the above vectors into a permissive cell, as this term is understood in the art (e.g., a "permissive" cell can be infected or transduced by the virus). Any method of introducing the vectors into the permissive cell may be employed, including but not limited to, electroporation, calcium phosphate precipitation, microinjection, cationic or anionic liposomes, and liposomes in combination with a nuclear localization signal.

Any suitable permissive mammalian cell known in the art may be employed to produce the chimeric adeno-parvoviruses of the invention, e.g., HEK 293, HEK 293Q, HEK293T, HEK293TT cells and any packaging cell line expressing the adenovirus E1 proteins. In a preferred embodiment of the method of the invention, the mammalian cells are HEK T-REx™-293 cells.

The present invention also provides a recombinant chimeric adeno-parvovirus vector obtainable by a method of the invention as well as a cell containing such vector.

Finally, the present invention also relates to a pharmaceutical composition containing the chimeric adeno-parvovirus vector of the invention and a pharmaceutically acceptable carrier as well as the use of a chimeric adeno-parvovirus vector of the invention for use in gene therapy or a method of treating a tumor. Suitable carriers and the formulation of such medicaments are known to the person skilled in the art. Suitable carriers may comprise e.g. phosphate-buffered saline solutions, water, emulsions, e.g. oil/water emulsions, wetting agents, sterile solutions, etc. The kind of carrier depends on how to administer the vector/virus according to the invention. A suitable dosage is determined by the attending physician and depends on various factors, e.g. the patient's age, sex and weight, the severity of the disease, the kind of administration, etc.

A gene therapy can be carried out with a chimeric adeno-parvovirus vector according to the invention, the cells being transduced/infected by incubation with the vector or viral particles. The cells may be present in an organism, the cells to be infected being reachable by needle injection, jet injection or particle gun. On the other hand, the cells to be transduced can also be isolated from an organism, be infected outside the organism and then be returned to the organism again. Such cells are referred to as autologous cells. Moreover, as to the organism it is also possible to use allogenic cells for the transduction. In this connection, it is favorable for these cells to belong to an HLA type corresponding to the organism. The person skilled in the art knows methods of providing cells with a certain HLA type. The recombinant vectors (particles) according to the invention are also useful for the adjuvant application to chemotherapy, i.e. to tumor therapy.

In summary, the inventors achieved to generate a chimeric adenovirus-parvovirus (Ad-PV) vector that combines the high-titre and efficient gene transfer of adenovirus with the anti-cancer potential of rodent parvovirus. To this end, in a most preferred embodiment the entire oncolytic PV genome was inserted into a replication defective E1 and E3 deleted Ad5 vector genome. As the inventors found that parvoviral NS expression inhibited Ad-PV chimera production, they engineered in a most preferred embodiment the parvoviral P4 early promoter, which governs NS expression, by inserting into its sequence tetracycline operator elements. As a result of these modifications, P4-driven expression was blocked in the preferred packaging T-REx™-293 cells, which constitutively express the tetracycline repressor, allowing high-yield chimera production. The chimera effectively delivered the PV genome into cancer cells, from which fully infectious replication competent parvovirus particles were generated. Remarkably, the Ad-PV chimera exerted stronger cytotoxic activities against various cancer cell lines, compared with the PV and Ad parental viruses, while being still innocuous to a panel of tested normal primary human cells. This Ad-PV chimera represents a novel versatile anti-cancer agent, which can be subjected to further genetic manipulations, in order to reinforce its enhanced oncolytic capacity through arming with transgenes or retargeting into tumour cells. Thus, the chimerical adenovirus-parvovirus vector of the invention is preferably to be used as a cancer therapeutic. Examples of targetable cancers are cervical carcinomas, gliomas, pancreatic carcinomas, melanoma, lung and colon cancers, including other cancers that are resistant to PV cytotoxicity.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example 1

Material and Methods (A) Cells

HEK 293 (transformed human embryonic kidney), NB324K (transformed newborn human kidney) and A549 (Lung carcinoma) cell lines were obtained from ATCC (LGS Standards GmBH, Wesel, Germany) and HEK T-REx™-293 from Invitrogen (Darmstadt, Germany). HeLa and SiHa cervical carcinoma cell lines, positive for human papillomavirus (HPV) type 16 and 18 respectively, were a gift from Dr. Angel Alonso (DKFZ, Heidelberg, Germany). The ME-180 cell line, positive for HPV 68, was obtained from Dr. Elisabeth Schwarz (DKFZ, Heidelberg, Germany). The early passage, cervical carcinoma derived cell cultures (CxCa), positive for HPV 16, were provided by Dr. Andreas Kaufmann (Charité-Medical University Berlin, Germany). The colon cancer HCT-15 and HCC-2998 and the Melanoma Lox-IMVI cell lines were from the National Cancer Institute (NCI) (Bethesda, Md., USA). The human primary oral fibroblasts and foreskin fibroblasts were a gift from Dr. Massimo Tommasino (IARC, Lyon, France). Human primary adult melanocytes, lightly pigmented (HEMa-LP), were from Invitrogen (Carlsbad, Calif., USA). Human astrocytes were obtained from ScienCell Research Laboratories (San Diego, Calif., USA).

HEK 293, HeLa, SiHa, CxCa, A549 and the human primary oral fibroblast cells were grown in Dulbecco's modified Eagle's (DMEM) medium supplemented with 10% foetal bovine serum (FBS) (Gibco, Invitrogen, Karlsruhe, Germany). T-REx™-293 cells were grown in DMEM containing 10% of tetracycline-free certified FBS (PAA, Colbe, Germany). ME-180 cells were grown in McCoy's 5a Modified Medium supplemented with 10% FBS, respectively. HCT-15, HCC-2998 and Lox-IMVI were grown in Roswell Park Memorial Institute (RPMI) 1640 medium complemented with 10% FBS. Human primary foreskin fibroblasts and NB324K were grown in Minimum Essential Medium (MEM) supplemented with 10% and 5% FBS, respectively. Primary human adult melanocytes were grown in medium 254 supplemented with HMGS (Invitrogen, Carlsbad, Calif., USA). Human astrocytes were cultivated in astrocytes medium (ScienCell Research Laboratories, San Diego, Calif., USA). All media, except the ones of the melanocytes and the astrocytes, contained 100 U/ml penicillin, 100 µg/ml streptomycin and 2 mM L-glutamine. Cells were grown at 37° C. in 5% $CO_2$ and 92% humidity.

(B) Viruses hH-1 and hH-1-TO viruses were produced in T-REx™-293 cells. The cells were cultivated in 10 cm dishes in tetracycline-free medium, and transiently transfected at 12.5% confluency with 10 µg/dish of either phH-1 or phH-1-TO viral constructs. At 4 h, 3 days and 6 days post transfection, dox (1 µg/mL) was added to the medium. At day 7, cells were harvested within their medium and lysed by 3 freeze-and-thaw cycles and cellular debris were removed by centrifugation. Produced viruses were further amplified by infecting NB324K cells and purified through iodixanol gradient centrifugation.

Ad-hH-1-TO and Ad control (Ad5ΔE1ΔE3) were produced through 3 rounds of production in T-REx™-293 cells cultivated in medium containing 5% tetracycline-free FBS. In the first round, cells in 12 well plates were transfected at 75% confluency with 1 µg/well of pAd-hH-1-TO or pAd5ΔE1ΔE3 plasmids pre-digested with PacI. After transfection, cells were induced or not with 1 µg/ml of dox. 5 days post-transfection, half of the culture medium was replaced, to ensure optimal growth conditions. 7 days post-transfection, cells were harvested into their medium, lysed with 3 freeze-and-thaw cycles and cellular debris were removed by centrifugation. In the second round, 25% of the crude viral extract produced in the first round were used to infect T-REx™-293 cells grown in 75 cm² flasks. 5 days post-infection, half of fresh medium was added to maintain optimal growth conditions. 7 days post-infection, cells were harvested and lysed as previously described. The third round was comparable to the second round but carried out in 175 cm² flasks. The final viral batches were purified twice through CsCl gradient ultracentrifugation.

(C) DNA Cloning

Figure 12A:
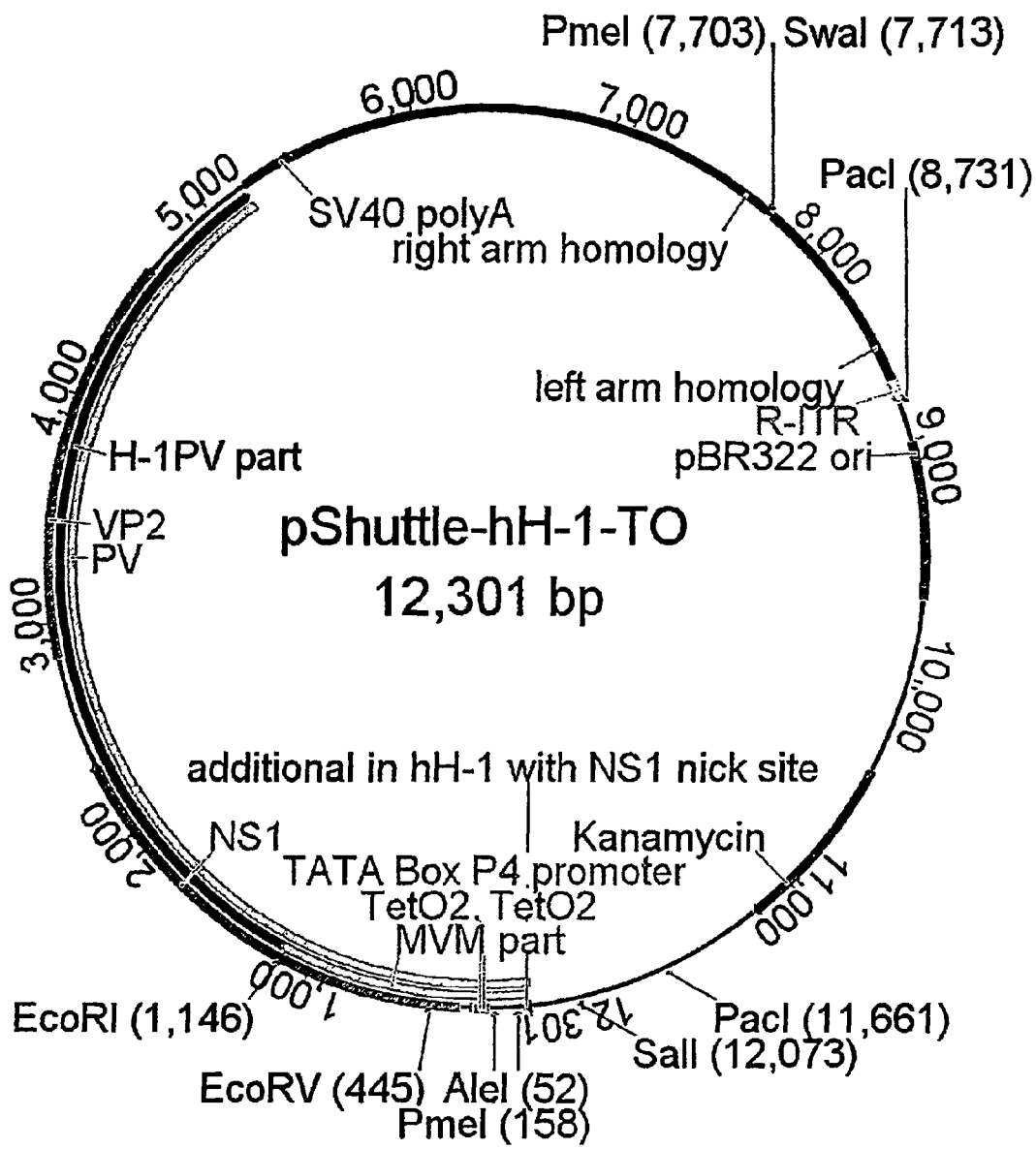
Figure 12B:
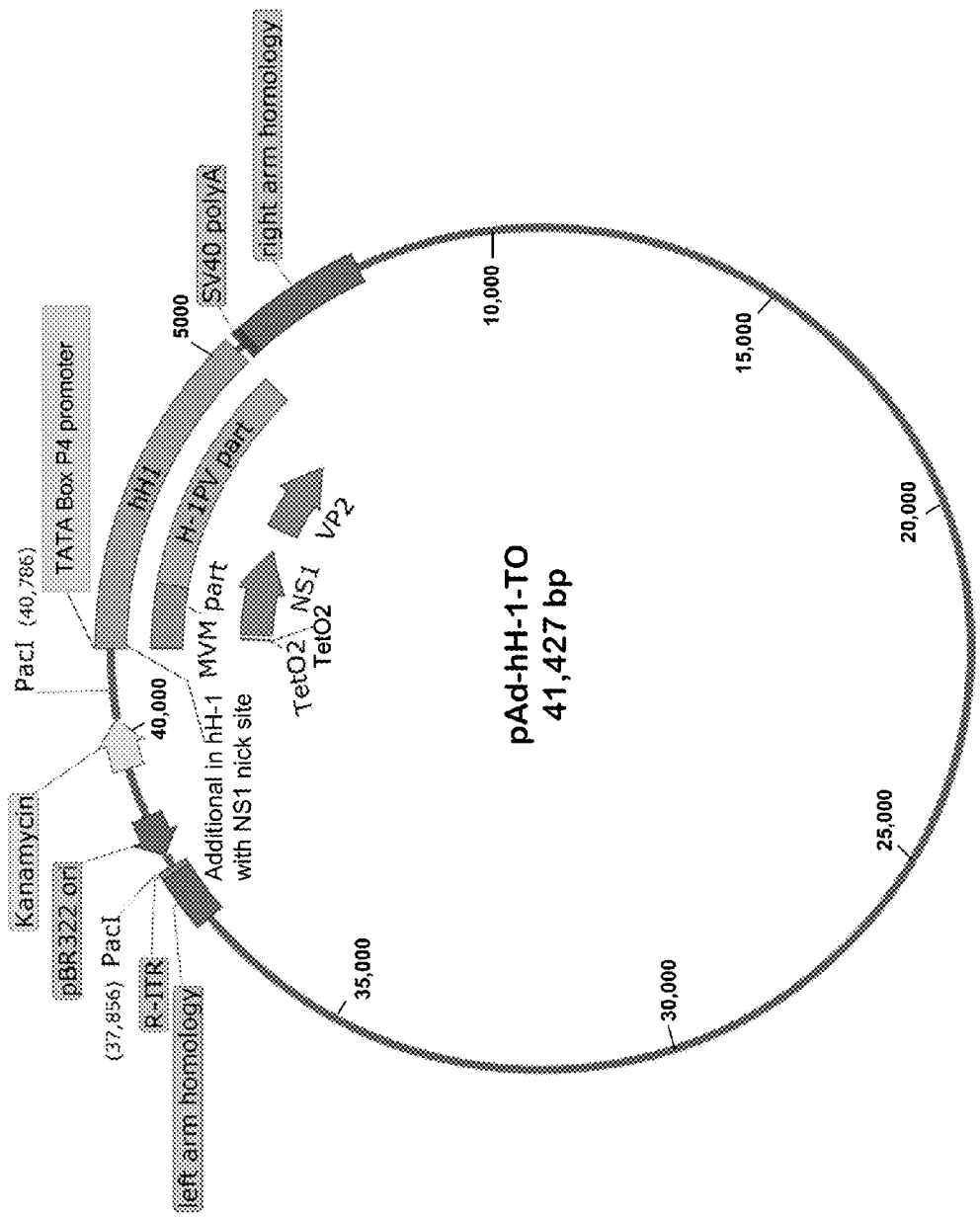

The phH-1-TO parvovirus plasmid was constructed by inserting two TetO₂ repressor elements into the P4 promoter of phH-1 [31], through PCR cloning. In a first step, two parallel PCRs were carried out, using phH-1 as a template, with the following primers: PCR1-For: 5'-AAACTCGAG-GCGGTTCAGGGAGTTTAAACC-3' and PCR1-Rev: 5'-AACTGACTTCTCTCTATCACTGATAGGGA-GATCTCTATCACTGATAGGGAAGTAGTT GCT-TATATACTTTAAACC-3'; PCR2-For: 5'-AGCAACTACT-TCCCTATCAGTGATAGAGATCTCCCTATCAGTGATA GAGAGAAGTCA GTTACTTATCTTTTCTTTC-3' and PCR2-Rev: 5'-AAAAAGCTTCCATCCGATATCTTTTC-CATTCAG-3'. In a second step, a third PCR was carried out using a stochiometric mix of the 2 previous purified PCR products as template with PCR1-For and PCR2-Rev as primers. The DNA product obtained was digested with PmeI/EcoRV and used to replace the corresponding fragment in phH-1.

pShuttle-CMV-free was constructed as follows: pShuttle-CMV (Qbiogen, MP Biomedicals, Heidelberg, Germany) was digested with Bg/II, dephosphorylated with Calf Intestine Phosphatase and subjected to homologous recombination, in E. coli BJ5183, with annealed oligonucleotides 5'-GTTCATAGCCCATATATGGAGTTCAGATCTGG-TACCG-3' and 5'-CGGTACCAGATCTGAACTC-CATATATGGGCTATGAAC-3'.

pShuttle-hH-1 was generated in 3 steps. (1) In pShuttle-CMV-free, the unique EcoRI site was changed into a SwaI site, through insertion of the annealed oligonucleotides 5'p-AATTATTTA-3' and 5'p-AATTTAAAT-3' at the EcoRI location. (2) The 5' region of hH-1 was amplified from phH-1 by PCR using the primers 5'-AAGGAAAAAAGTC-GACTTTTGTGATGCTCGTCA-3' and 5'-AG-GAAAAAAGATATCTTTTCCATTCAGTTGA-3'. The PCR product was digested by SalI/EcoRV (633 bases) and ligated into the previously modified pShuttle-CMV-free vector, pre-digested with the same enzymes, resulting in the pShuttle-5'hH-1. (3) The remaining 3' end of the hH-1 genome (4730 bases) was excised from the phH-1 plasmid using the EcoRV/NdeI enzymes, Klenow blunted and ligated in the EcoRV digested pShuttle-5'hH-1, generating the pShuttle-hH-1.

pShuttle-hH-1-STOP was cloned by inserting 3 X STOP-codons into the unique EcoRV site of the pShuttle-hH-1, located at the beginning of the parvovirus NS coding sequence. The 3XSTOP DNA duplex was generated by the self-annealing of the oligonucleotide 5'-TAATAGT-GAGAATTCTCACTATTA-3'.

pShuttle-hH-1-TO (FIG. 12A) was obtained by substituting the AleI/EcoRV fragment of pShuttle-hH-1 with the corresponding 393 bases-long DNA fragment from phH-1-TO.

pAd-hH-1, pAd-hH-1-STOP and pAd-hH-1-TO (FIG. 12B) were generated by recombination of pShuttle-hH-1, pShuttle-hH-1-STOP or pShuttle-hH-1-TO, respectively, with pAd5ΔE1ΔE3 into E. coli BJ5183, according to the AdEasy™ Adenoviral Vector System instruction manual (Agilent technologies, Stratagene products, Waldbronn, Germany).

pAd5ΔE1ΔE3, in which the regions encompassing the E1 (nt 459 to 3228) and E3 (nt 27897 to 30463) genes (Ad5 Refseq: AC_000008) were deleted, was constructed as follows. A shuttle plasmid containing E3 flanking sequences [32] was digested by MluI/XbaI, blunted with Klenow and ligated generating pLeft-Right. This plasmid, was SalI/NotI digested, dephosphorylated and used for homologous recombination in *E. coli* BJ5183, with SpeI-linearized pTG3622 [33] from which the E1 region has been deleted.

All the constructs hereby described were clonally isolated and their full-length sequences verified.

(D) Transfections

DNA transfections were carried out using Fugene HD (Roche Diagnostics & Applied Sciences, Mannheim, Germany) according to the manufacturer's instructions with minor modifications. Plasmids were diluted in serum-free medium to a final concentration of 20 ng/µl. Fugene HD was then added with a 1:2.5 ratio (µg DNA:µl Fugene) and the mixture was incubated at RT for 30-60 min. Subsequently, the mixture was added to the cells dropwise.

(E) Protein Extraction

Cellular pellets were lysed on ice for 30 min in 5 volumes of protein extraction buffer (50 mM Tris pH 8, 200 mM NaCl, 0.5% NP-40, 1 mM DTT) containing protease inhibitors (complete EDTA-free, Roche, Mannheim, Germany) and 10% glycerol. Cell debris was removed by centrifugation at 10.000 RPM for 10 min at 4° C.

(F) Antibodies

The following antibodies were used for Western blot analysis: mouse monoclonal anti-β-tubulin (clone TUB 2.1, Sigma-Aldrich, Saint Louis, Mo., USA), mouse monoclonal anti-actin (Clone C4, MP Biomedicals, Illkirch, France), polyclonal anti-NS1 SP8 antiserum (provided by Dr. Nathalie Salomé, ATV-DKFZ, Heidelberg, Germany) [34] and polyclonal anti-VP2 antiserum (a gift from Dr. Christiane Dinsart, ATV-DKFZ, Heidelberg, Germany) [31].

(G) Parvovirus Titration (1) Plaque Assay

NBK cells grown at a density of 20,000 cell/cm$^2$ were infected with serial dilutions of crude virus extracts for 1 h, followed by replacement of the inoculum with an overlay of 0.68% Bacto™ Agar (Becton Dickinson GmbH, Heidelberg, Germany) in Minimum Essential Medium (Gibco, Invitrogen) supplemented with 5% FBS, 2 mM L-Glutamine, 100 U/ml Penicillin, 100 µg/ml Streptomycin. 7 days post-infection, living cells were stained for 18 h with an overlay of neutral-red (0.2 mg/ml) containing Bacto™-agar (0.85%) diluted in PBS. Plaques were counted and titers were expressed as plaque-forming units (PFU) per ml.

(2) Quantitative Real Time Polymerase Chain Reaction (qPCR)

Crude virus extracts were digested with 50 U/ml of Benzonase® Nuclease [Ultrapure grade, (Sigma-Aldrich Chemie GmbH, Steinheim, Germany)] for 30 min at 37° C. to remove free viral genomic DNA. To release viral DNA from viruses, 10 µl of each sample were lysed in a total of 40 µl of alkaline lysis buffer (1 M NaOH in TE buffer) at 56° C. for 30 min. Lysis was stopped by adding 960 µl of 40 mM HCl. Quantification of viral DNA was carried out by real-time qPCR with a NS1-specific TaqMan™ probe (Applied Biosystems, Darmstadt, Germany), as previously described [28]. With this method, it was calculated that 1 PFU of hH-1-TO and 1 Ad X U (see below) of Ad-hH-1-TO was corresponding to approximately 500 and 100 viral genome containing particles, respectively.

(H) Adenovirus Titration

Recombinant adenovirus titres were determined using the Adeno-X™ Rapid Titer Kit (Clontech, Saint-Germain-en-Laye, France), 3 days after infection of T-REx™-293 cells (Invitrogen) and expressed as Ad X unit/ml.

The concentration of adenovirus physical particles was estimated from the DNA content of the purified viruses, measured through the absorbance at 260 nm. An absorbance of 1 corresponds to $1.1 \times 10^{12}$ adenovirus particles per ml [35].

(I) Electron Microscopy

Carbon-coated 300-mesh copper grids were placed face down onto 5 µl aliquots of virus suspension for 2 min, stained with 2% uranylacetate for 30 s, and dried for approx. 1 min. Micrographs were taken at a magnification of 38,000-fold with a Zeiss 10A transmission electron microscope (Zeiss, Oberkochen, Germany) using an acceleration voltage of 80 kV. The magnification indicator was routinely controlled by comparison with a grating replica.

(J) Lactate Dehydrogenase (LDH) Assay and MTT Assays

Human cells were first seeded in 96 well plates, at densities of 4000 cells/well for cancer cells and 8000 to 10000 cells/well for primary cells. Exceptionally, melanocytes and astrocytes were grown in artificial mediums (indicated in (A)), then were seeded in DMEM medium supplemented with 10% heat inactivated FBS. After infection, all cells were kept in their corresponding basal medium supplemented with 5% of heat-inactivated bovine serum, with 200 µl volume per well. Cancer cells and primary cells were incubated for 4 and 5 days respectively, then were assayed for LDH and MTT as previously described [13].

LDH were measured using CytoTox 96 nonradioactive cytotoxicity assay (Promega Biotech, Madison, Wis., USA) and read by an ELISA reader at 492 nm. After subtraction of the background value given by non conditioned medium, the fraction of lysed cells in infected or non infected cultures was calculated from the ratio of the LDH activity in the conditioned medium to the total LDH activity of the corresponding culture. The total LDH activity was determined after cell lysis by the addition of 10× buffer containing 9% (vol/vol) Triton X-100. The same cell cultures were used to determine LDH release and MTT activity. MTT activity (3-(4,5-dimethylthiazol-2-yl)-2,5-diphenyl-2H-tetrazolium bromide) (Sigma-Aldrich Chemie GmbH, Steinheim, Germany) was read with an ELISA reader at 570 nm. The viability of infected cells was expressed as the ratio of the corresponding absorbance to that of non infected cells taken arbitrarily as 100%.

(K) Real-Time Detection of Viral Cytopathic Effect (CPE)

Cells were seeded on 96-well E-Plate (Roche Diagnostics Deutschland GmbH, Mannheim, Germany) with a density of 4000 cells/well (unless for HCC-2998: 8000 cells/well). 24 h to 72 h later, cells were infected with Ad-hH-1-TO, Ad5ΔE1ΔE3 (Ad control), hH-1-TO or the combination of the Ad control and hH-1-TO viruses. Cellular proliferation, reflecting virus-mediated cytopathic effect (CPE), was monitored in real time, every 30 min, using the xCELLigence System (Roche Diagnostics Deutschland GmbH, Mannheim, Germany). The growth curves shown represent the average of at least three replicates with relative standard deviations.

Example 2

Generation of Parvovirus hH-1-TO Carrying a Tetracycline Inducible P4 Promoter

Figure 2A:
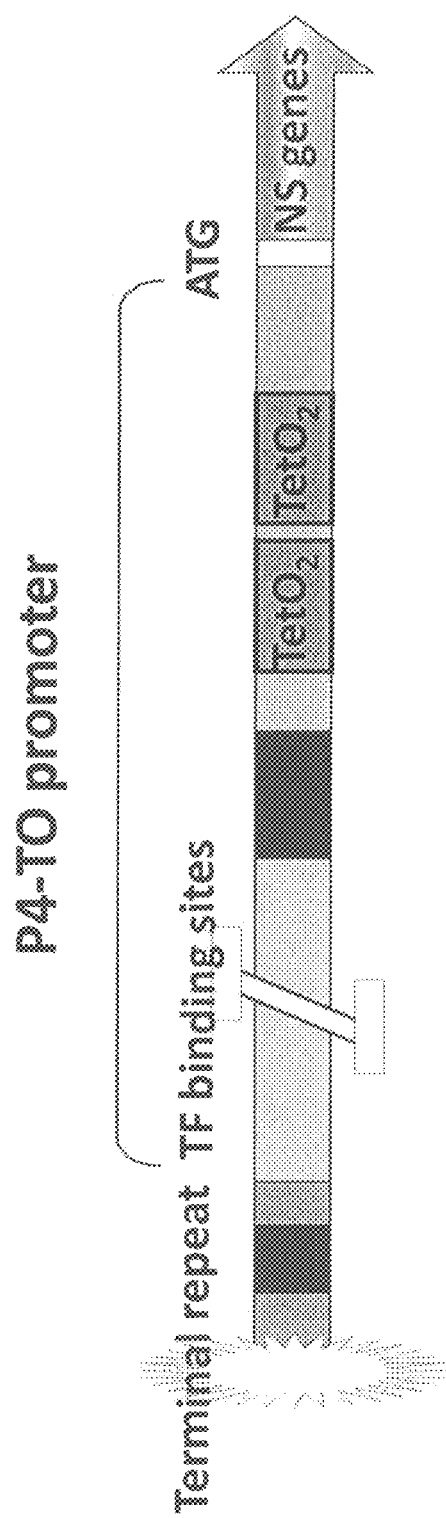
FIG. 2A-2B: Construction of an inducible parvovirus P4 promoter (P4-TO). (A) Schematic view of the P4-TO promoter generated by inserting two tetracycline operator 2 (TetO$_2$) elements into the P4 promoter from the hH-1 genome (SEQ ID NO. 10). TF: transcription factors. (B) DNA sequence of the P4-TO promoter. The TATA box, the two TetO$_2$ elements and the NS translation ATG start codon are highlighted.
Figure 2B:
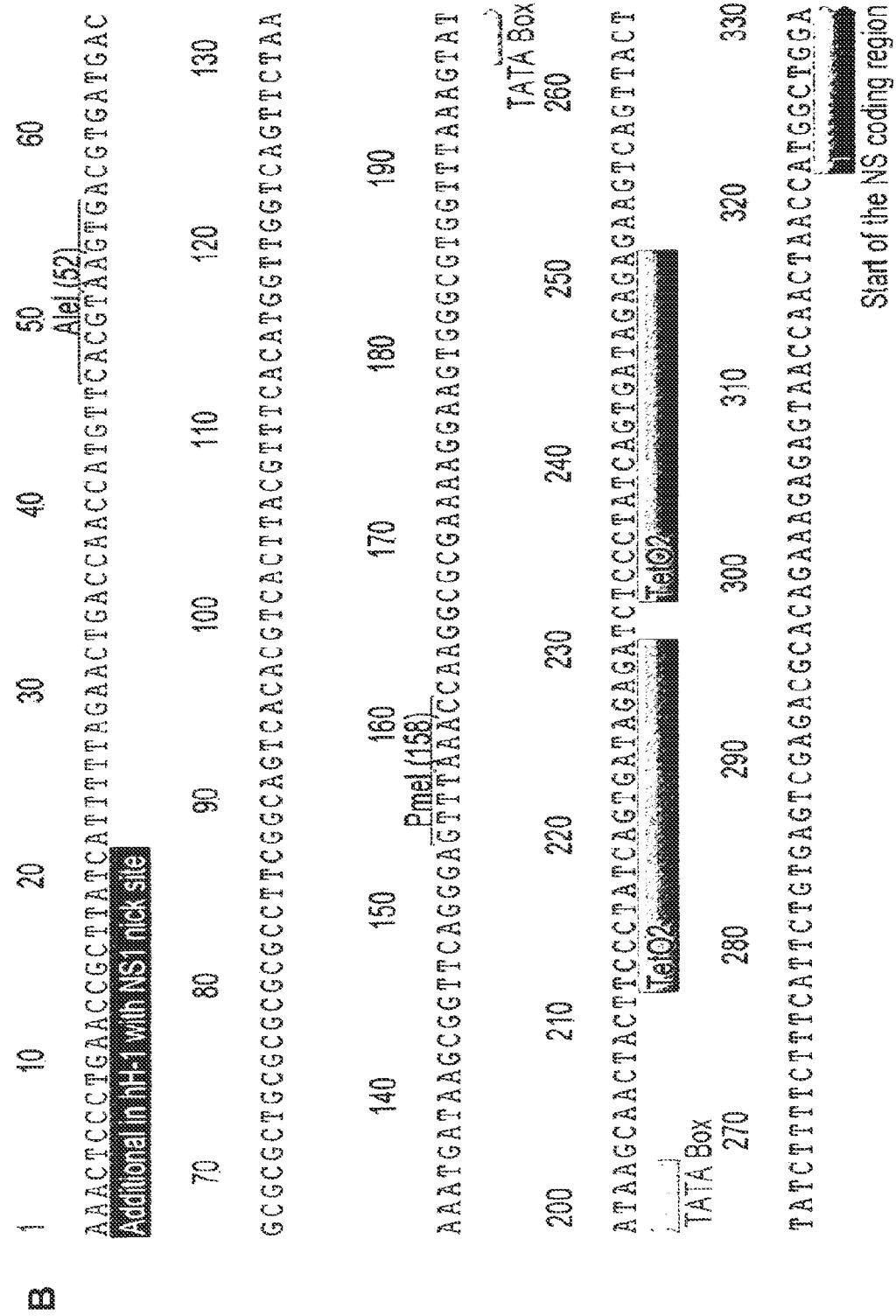

First attempts aiming to produce Adenovirus carrying a chimeric Ad-PV genome failed for the fact that parvovirus NS proteins (most likely NS1) interfered with Ad-PV chimera production (FIG. 1). Indeed, the introduction of stop codons within the NS open reading frame could rescue Ad production to normal levels (FIG. 1). In view of these results, the parvovirus early P4 promoter, which controls the expression of the NS gene, was modified in order to tightly control its activity during chimera production. Advantage of the T-REx™ technology [29, 30] was taken and it was tested whether it was possible to engineer the P4 promoter and make it inducible by inserting two tetracycline operator 2 elements (TetO2) [30] between the TATA box and the NS starting codon (FIGS. 2A and B). With this modification, the P4 promoter activity was expected to be repressed in T-REx™-293 cells, constitutively expressing the tetracycline repressor (TetR), in the absence of doxycycline (dox) and induced in its presence [30]. On the contrary, in cancer cells which do not express the TetR, the P4 promoter should be fully functional. This modified parvovirus was generated from an infectious molecular clone and named phH-1-TO (FIG. 2).

Figure 3:
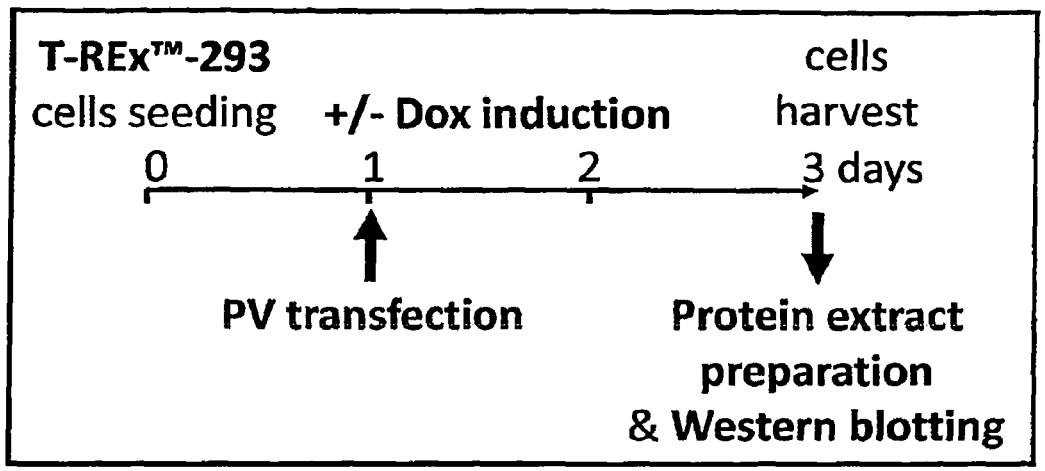
FIG. 3: Inducibility of phH-1-TO plasmid containing the P4-TO promoter. (A) Experimental design. T-REx™-293 cells, constitutively expressing the Tet repressor, were transfected with either phH-1 or phH-1-TO molecular clones and grown in a medium with (+) or without (−) dox (1 µg/ml). After 48 h, total protein cell extracts were prepared from these cultures and analyzed by Western blotting for the presence of viral proteins (NS1 and VP) and actin (used as a loading control). (B) Western blots showing that viral gene expression responds to dox induction. Proteins were separated by SDS-PAGE.
Figure 3:
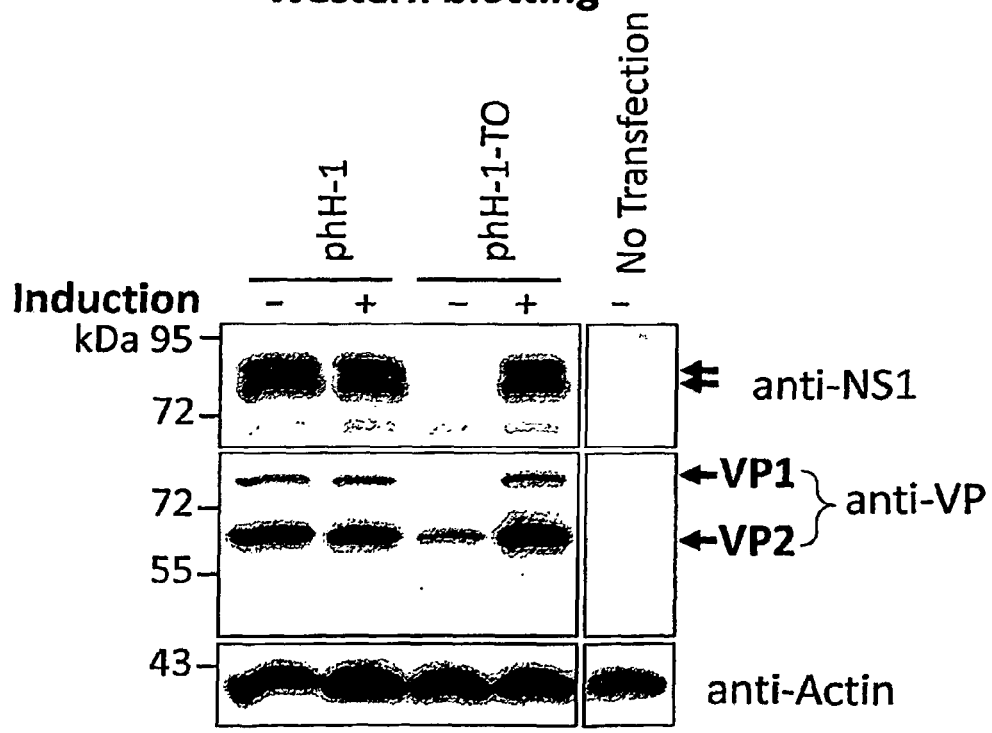

In order to verify whether the expression of the parvoviral proteins from phH-1-TO is inducible as anticipated, T-REx™-293 cells were transfected with phH-1-TO or parental phH-1, incubated for 2 days, harvested and processed for Western blotting detection of parvoviral NS1 and VP proteins (FIG. 3A). In cells transfected with the parental phH-1 viral vector, the addition of dox did not affect total NS1 protein levels (FIG. 3B). On the contrary, phH-1-TO-transfected cells, detection of NS1 was observed only in the presence of dox, demonstrating that the activity of P4-TO promoter is under control of an ON/OFF switch mechanism. Under induction conditions, NS1 protein levels were similar to the ones achieved using the parental viral vector, indicating that the insertion of the TetO$_2$ did not impair NS production when dox was supplied to the cultural medium. It is known that the NS1 protein transactivates the parvoviral p38 promoter, which controls the transcription of the VP genes coding for the capsid proteins. In agreement with the repression of NS1 production, only a slight expression of VP1 and VP2 was observed in phH-1-TO transfected T-REx™-293 cells grown in doxycycline-free conditions. In contrast, VP proteins accumulated in these cells when dox was added to the medium (FIG. 3B).

Figure 4:
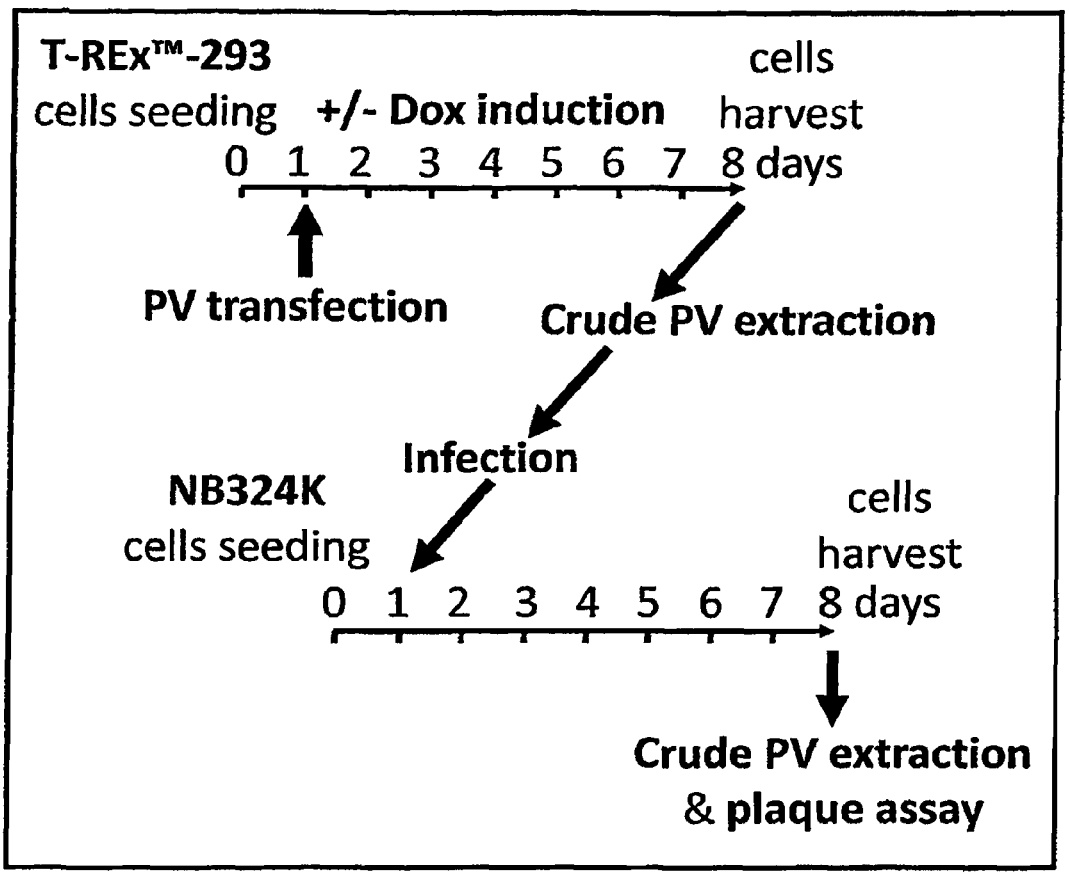
FIG. 4: Infectiousness of the hH-1-TO virus. (A) Experimental design. T-REx™-293 cells were transfected with either phH-1 or phH-1-TO viral plasmids and grown for one week in the presence or absence of dox. Cells were harvested within their medium and lysed. Produced viruses were further amplified by infecting NB324K cells. Cell lysates from these cultures, were then analyzed for the presence of parvovirus particles by plaque assay on NB324K indicator cells. (B) Representative images (5 cm diameter areas) from the plaque assay.
Figure 4:
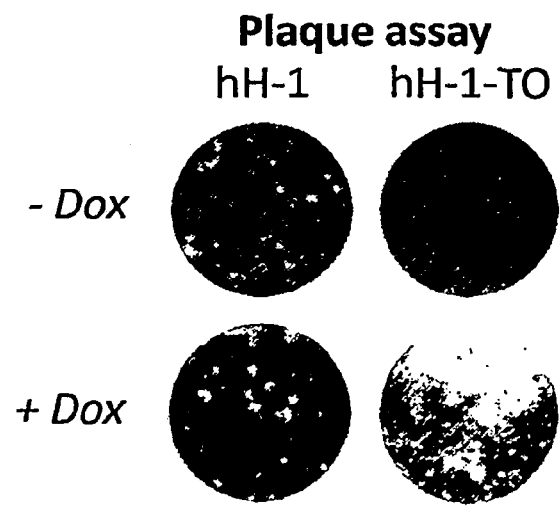

Next it was investigated whether transfection with phH-1-TO resulted in the production of infectious progeny virions. For this purpose, T-REx™-293 cells were transfected with phH-1-TO or phH-1 constructs and grown in the presence or absence of dox for a total of 7 days. Cell lysates from these cultures were then used for the infection of NB324K cells. After additional 7 days, cells were again lysed and crude cellular extracts tested for the presence of full virions able to infect, kill and spread in NB324K indicator cells, as measured by a plaque assay (FIG. 4A). As expected, the parental hH-1 virus was produced at similar levels irrespective of the presence of dox. On the contrary, dox was required during the T-REx™-293 transfection phase for hH-1-TO virions to be produced at a significant level (FIG. 4B), yielding virus titers comparable to the ones obtained with the parental virus. These results show that TetO$_2$ insertions into the P4 promoter-region (i) make PV production in the T-REx™-293 cells dependent on dox-induction and (ii) are fully compatible with the entire course of parvovirus life cycle since in cells like NBK324 that do not express the TetR the de novo generated hH-1-TO viral particles are fully infectious and capable to autonomously replicate.

Figure 5:
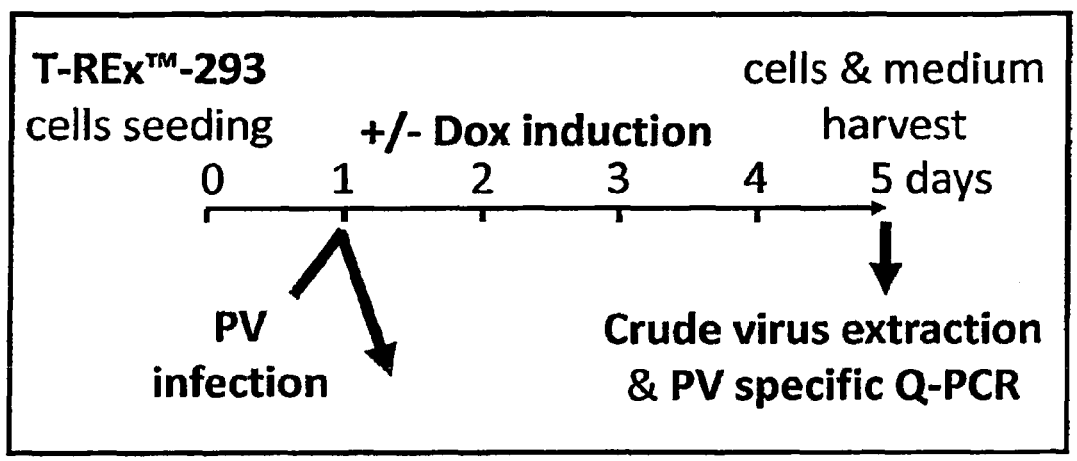
FIG. 5: Dox-dependence of hH-1-TO virus replication in T-REx™-293 cells. (A) Experimental flowchart. T-REx™-293 cells, grown in 6 well plates, were infected with hH-1 or hH-1-TO viruses, at a multiplicity infection of 2500 viral genomes Vg per cell, and further grown in the presence or absence of dox. After 4 days, cells were harvested within their medium and lysed with 3 freeze and thaw cycles. After elimination of cellular debris by centrifugation, crude virus preparations were treated with benzonase to remove free viral DNA and processed for parvovirus specific qPCR. (B) qPCR results of hH-1 or hH-1-TO parvoviruses, as expressed in Vg/ml.
Figure 5:
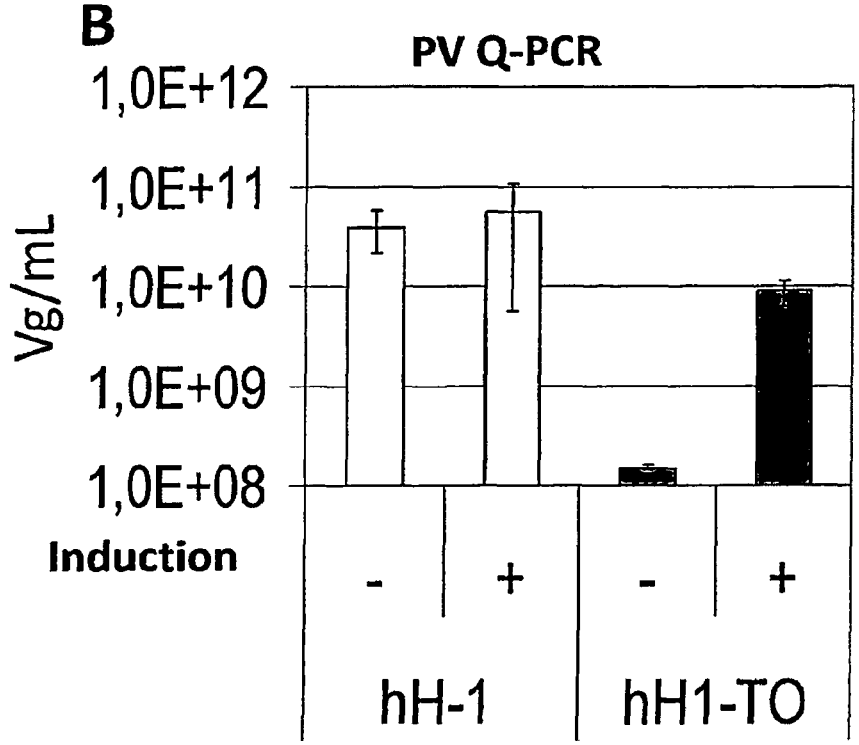

The propagation of hH-1-TO viruses was further investigated in T-REx™-293 cells. Cells were inoculated with either hH-1-TO or hH-1 viruses and grown in the presence or absence of dox for 4 days with one medium change at 24 h in order to eliminate unbound viral particles. Cells were then lysed into their media, and the parvovirus production was evaluated by a parvovirus-specific qPCR (FIG. 5A). In agreement with the results presented above, production of hH-1-TO virus in T-REx™-293 cells was only efficient when cultures were grown in the presence of dox, with a 60 fold reduction of virus titres in the absence of the inducer (FIG. 5B). It should be noted, however, that the production of hH-1-TO in the presence of dox was about six fold lower than that of hH-1, suggesting that the modifications introduced into the P4 promoter region slightly reduced the fitness of the virus in these cells.

Example 3

Generation of the Adeno Parvo Chimera

Figure 6:
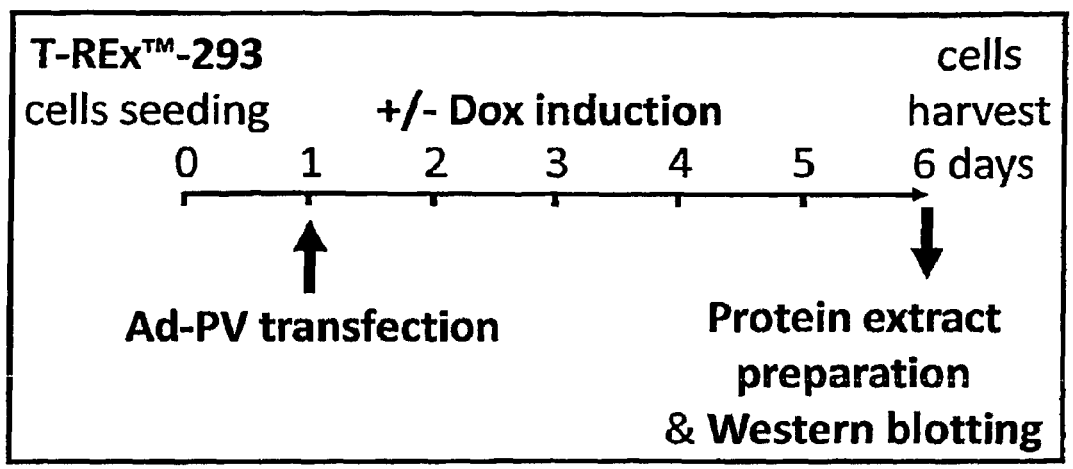
FIG. 6: Inducibility of the chimeric pAd-hH-1-TO plasmid. (A) Experimental flowchart. T-REx™-293 cells were transfected with pAd-hH-1-TO plasmid and further grown in medium with or without dox for 5 days. Cells were then lysed and total protein extracts analyzed by Western blotting for the presence of parvovirus NS1 and VP proteins, and β-tubulin (loading control). (B) Representative images of the Immunoblots. Proteins were resolved by 8% SDS-PAGE.
Figure 6:
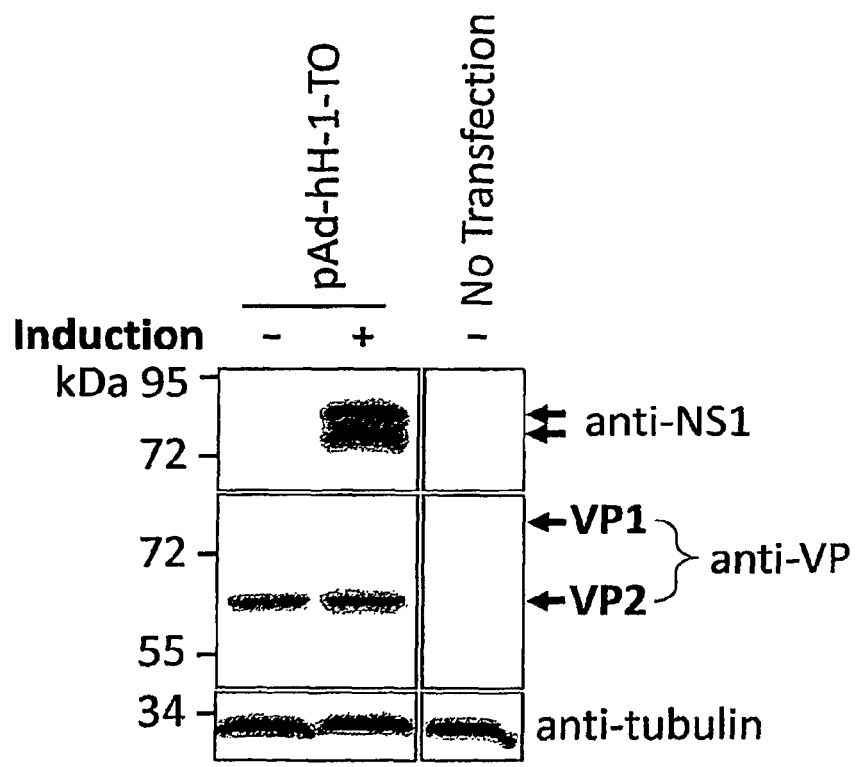

Due to the results presented in Example 2 the entire parvovirus hH-1-TO genome was inserted into the DNA backbone of a replication deficient adenovirus vector (Ad5ΔE1ΔE3), thus generating the pAd-hH-1-TO chimeric vector. First, it was tested whether the P4-TO promoter region kept its TetR-sensitivity once inserted into the Ad genome. For this purpose, T-REx™-293 cells were transfected with the pAd-hH-1-TO chimeric vector and grown for 5 days with or without dox. Total protein extracts from these cells were then analyzed by Western blotting for the presence of the parvoviral NS1 and VP proteins (FIG. 6A). As illustrated in FIG. 6B, NS1 was detected only when dox was provided to the cells. Consistent with previous results (FIG. 3B), NS1 expression correlated with an induction of the VP1 and VP2 capsid protein expression. These results confirmed the Tet-R-sensitivity of P4-TO gene expression in an Ad context.

Figure 7:
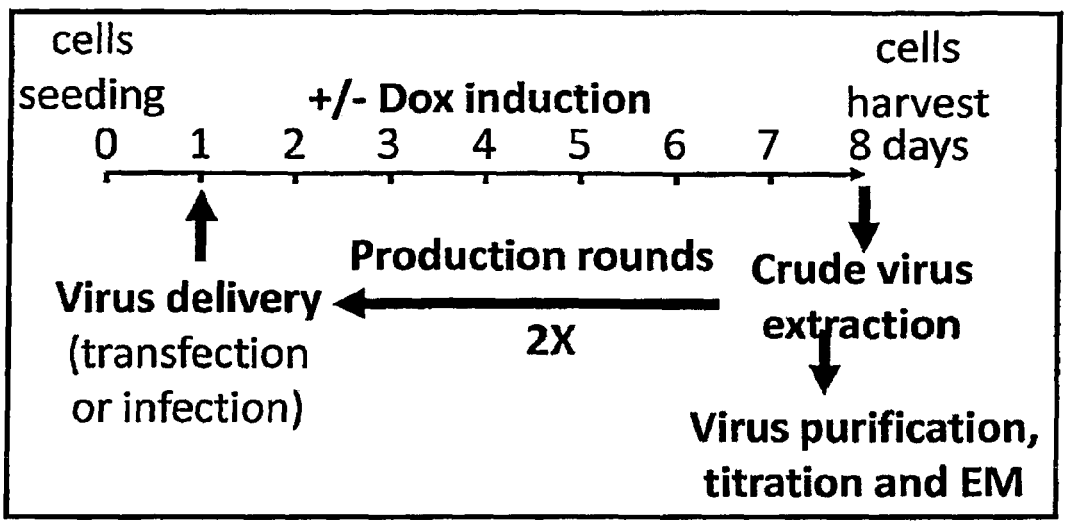
FIG. 7: Adeno-parvovirus chimera production. (A) Experimental flowchart. In a first round of production, T-REx™-293 cells were transfected with the chimeric plasmid pAd-hH-1-TO or the parental plasmids pAd (pAd5ΔE1ΔE3) or phH-1-TO, and grown in a medium supplemented (or not) with dox. Cell lysates from these cultures were used for infection of fresh T-REx™-293 cells in a second round of production and the procedure was repeated a third time by scaling-up the volume of the culture flasks as described in Example 1. Viral stocks were purified twice through CsCl gradient ultracentrifugation and characterized. (B) Virus preparations were titrated using the Adeno-X™ Rapid Titer Kit (Clontech) and are expressed as Ad X units/ml. (C) Electron microscopy images of the purified Ad-hH-1-TO Ad and hH-1-TO viruses. The solid bar represents a length of 100 nm.
Figure 7:
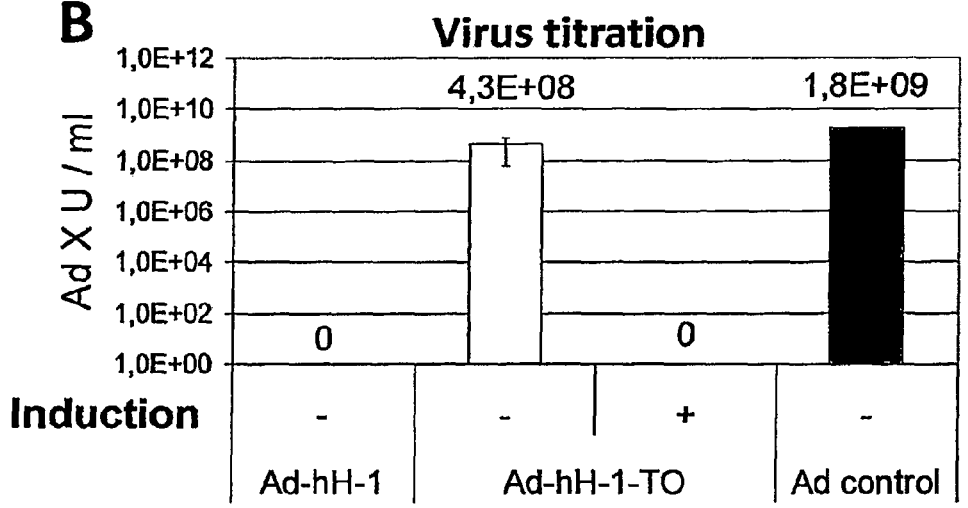
Figure 7:
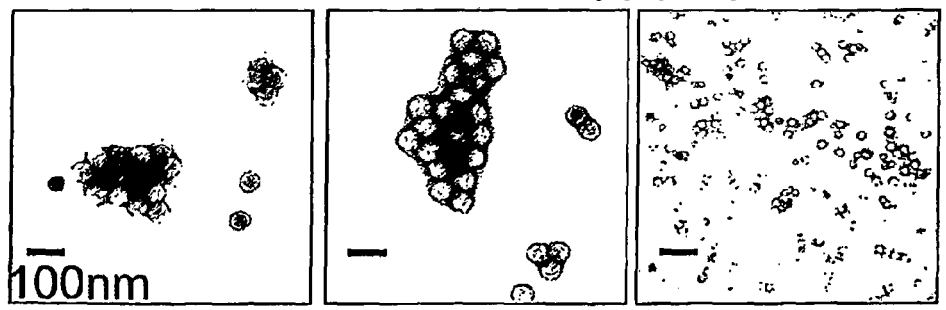

Next, it was investigated whether it was possible to produce Ad-PV chimeric virions from the pAd-hH-1-TO construct. As a negative control, the pAd-hH-1 vector containing the wild type P4 promoter (from which we previously failed to generate the chimeric virions) (FIG. 1) was used, and as positive control, the parental Ad plasmid whose E1/E3 gene deletion is complemented by the 293 cells used as producers. In a first round of production, T-REx™-293 cells were transfected with either pAd-hH-1-TO, pAd-hH-1 or pAd plasmids and grown in a medium containing (or not) dox for 7 days before being lysed. Crude cell extracts were then used to re-infect fresh T-REx™-293 cells in two successive rounds of virus amplification (FIG. 7A). The final cell lysates were then purified by cesium chloride (CsCl) gradient centrifugation and the viral stocks titrated using an adenovirus replication assay. Virus preparations were also subjected to electron microscopy analysis to control their purity. In agreement with previous results (FIG. 1), the pAd-hH-1 chimeric vector failed to generate any detectable viral particles. In contrast, Ad-hH-1-TO chimeric viruses were produced in T-REx™-293 cells, unless dox was added to the culture medium. These results were in line with above evidence that parental NS proteins (most likely NS1), were responsible for the inhibition of adenovirus chimeric virus replication. Remarkably, the production of the Ad-hH-1-TO chimeric viruses was not only possible in the presence of functional TetR but also very efficient as it was within the yield range of Ad control (FIG. 7B). Electron microscopy analysis showed neither differences between Ad-hH-1-TO and Ad-control viruses, nor parvovirus contamination in the produced Ad-hH-1-TO viral stocks (FIG. 7C). Taken together, these results demonstrate that by transiently blocking the parvoviral NS transcription unit, it is possible to produce Ad-PV chimeric viruses at high titers in the T-REx™-293 packaging cell line.

Example 4

Rescue of Infectious Parvovirus from the Adeno/Parvo Chimera

Figure 8:
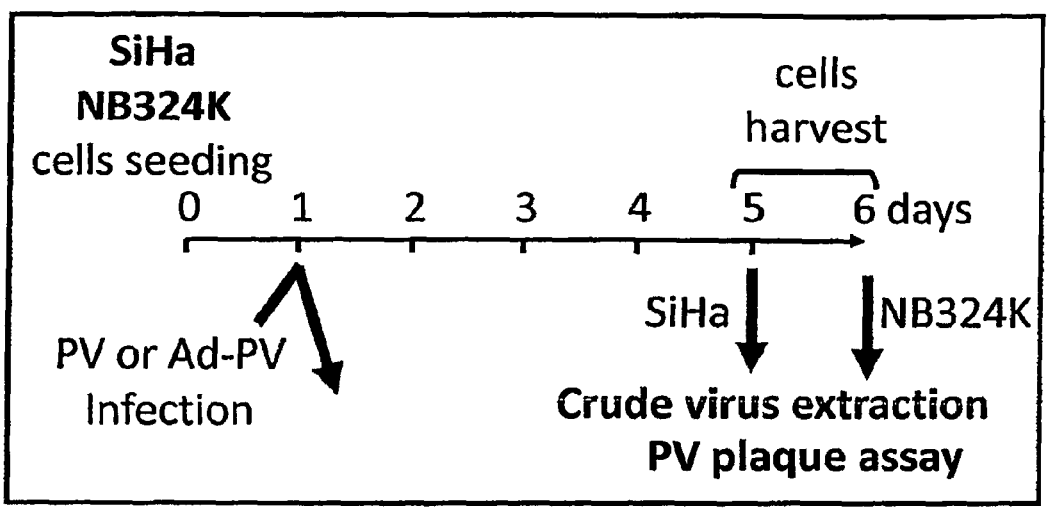
FIG. 8: Rescued and production of progeny parvoviruses in cells infected with the Ad-hH-1-TO chimera. (A) Experimental flowchart. SiHa and NB324K cells were infected with hH-1-TO or Ad-hH-1-TO viruses and culture media were renewed after 1 day to remove unbound viruses. After further incubation for 4 to 5 days, cells were harvested within their medium and lysed. Crude virus preparations were analyzed for the presence of parvoviruses by plaque assay. (B) Parvovirus produced in SiHa and NB324K cells infected with Ad-hH-1-TO or hH-1-TO viruses at indicated MOI, were quantified. Parvovirus titres are expressed in PFU/cell.
Figure 8:
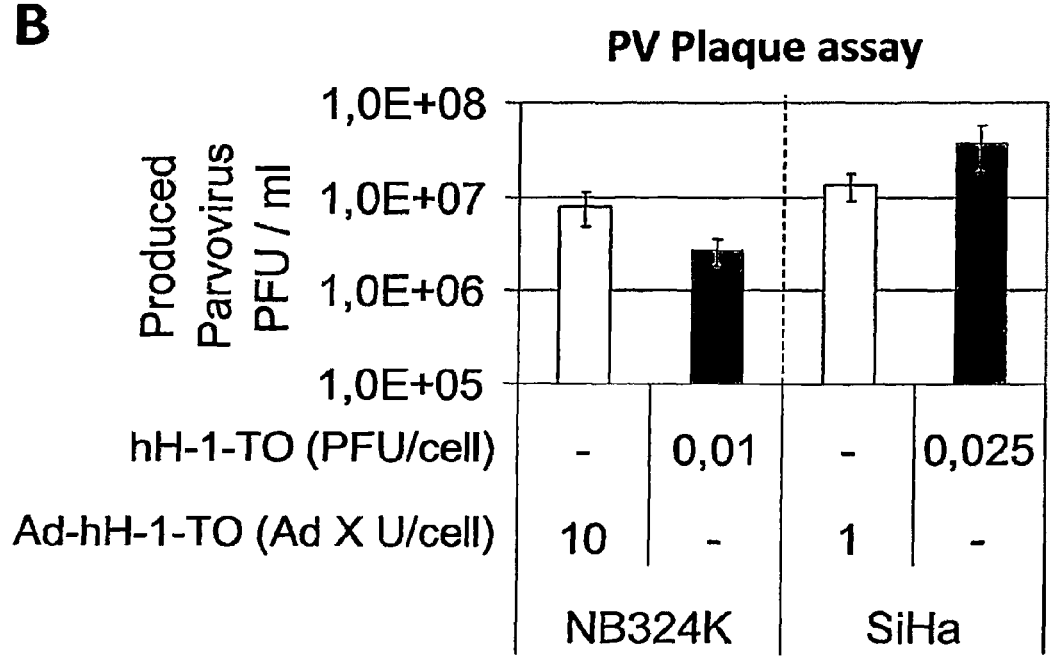

Then it was investigated whether it is possible to generate fully infectious parvoviruses by infecting transformed target cells with Ad-hH-1-TO chimeric viral particles. Two cell lines permissive for parvovirus production, namely the cervical carcinoma-derived SiHa and SV40-transformed NB324K, were infected with purified Ad-hH-1-TO or hH-1-TO viruses and incubated for 4 (SiHa) or 5 (NB324K) days, with one renewal of culture medium after 24 h to remove unbound viruses. Infected cells were then lysed into their medium, and crude extracts analyzed for the presence of infectious parvovirus particles by plaque assay (FIG. 8A). Verifying the initial working hypothesis, autonomously replicating infectious parvoviruses were rescued upon infection of both NB324K and SiHa cells with Ad-hH-1-TO chimeric virions (FIG. 8B). These results provide proof-of-concept that the Ad-PV chimera can be used as a novel tool for the delivery of autonomous parvoviruses to target cells.

Example 5

Enhanced Oncolytic Potential of the Ad-hH-1-TO Chimera

It is known that H-1PV induces cytopathic effects (CPE) on a large number of cancer cells [10]. Preliminary experiments showed that the hH-1 and hH-1-TO parvoviruses had similar cytotoxic activities against HeLa cells indicating that the modification introduced into the P4 promoter region did not modify the oncolytic activity of the virus.

Figure 10:
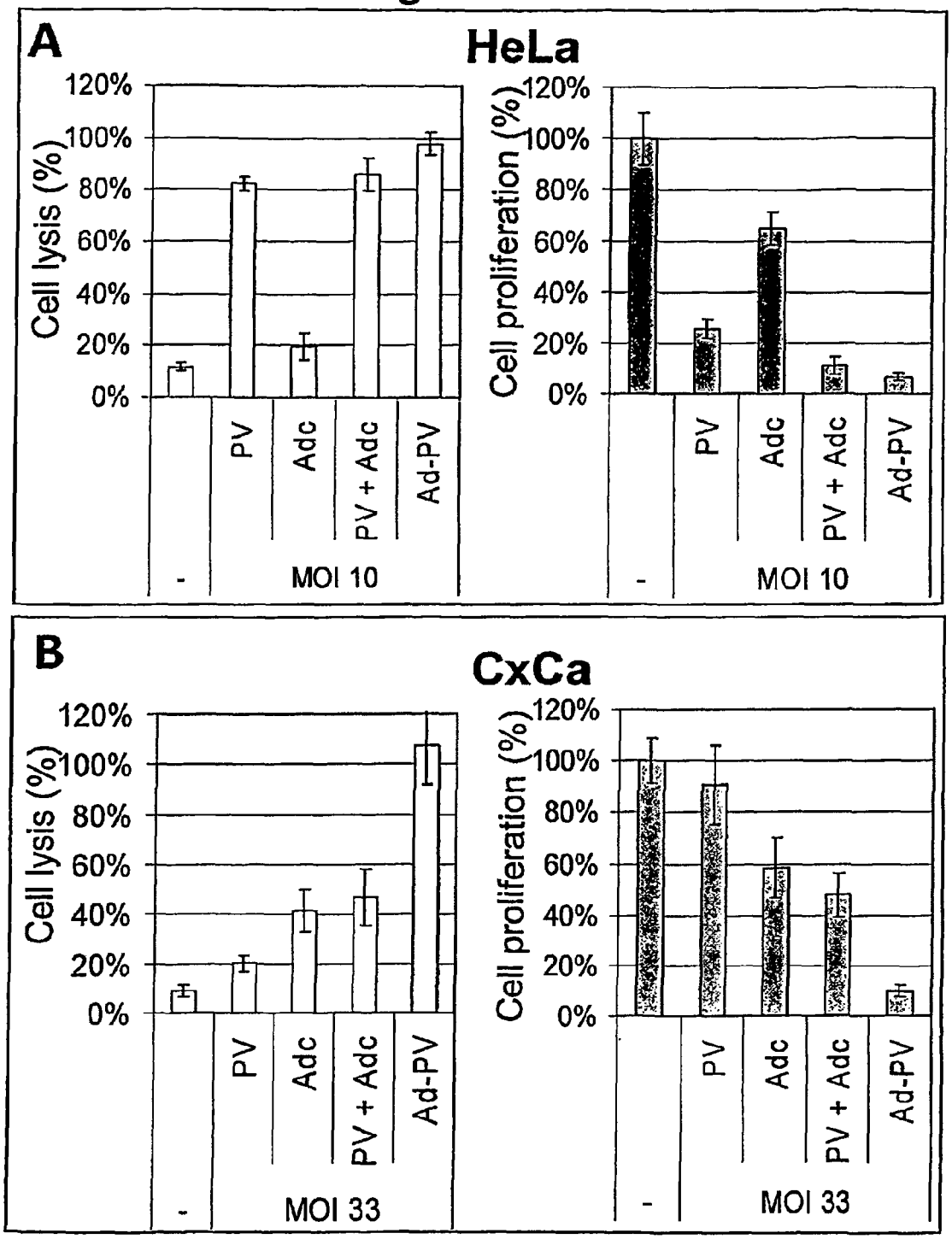
FIG. 10: The Ad-hH-1-TO chimera has improved oncolytic_activities with respect to its parental viruses. Cervical carcinoma derived HeLa (A), CxCa (B), ME-180 (C), melanoma LOX-IMVI (D), colon cancer HCT-15 (E) and HCC- 2998 (F) were seeded in 96 well plates, and infected or not (−) with chimeric Ad-hH-1-TO (Ad-PV), Ad control (Adc), hH-1-TO parvovirus (PV) or a mixture of Ad control and hH-1-TO viruses (PV+Adc). After 4 days of incubation, cell lysis and cell proliferation were assessed by LDH and MTT assays, respectively.
Figure 10:
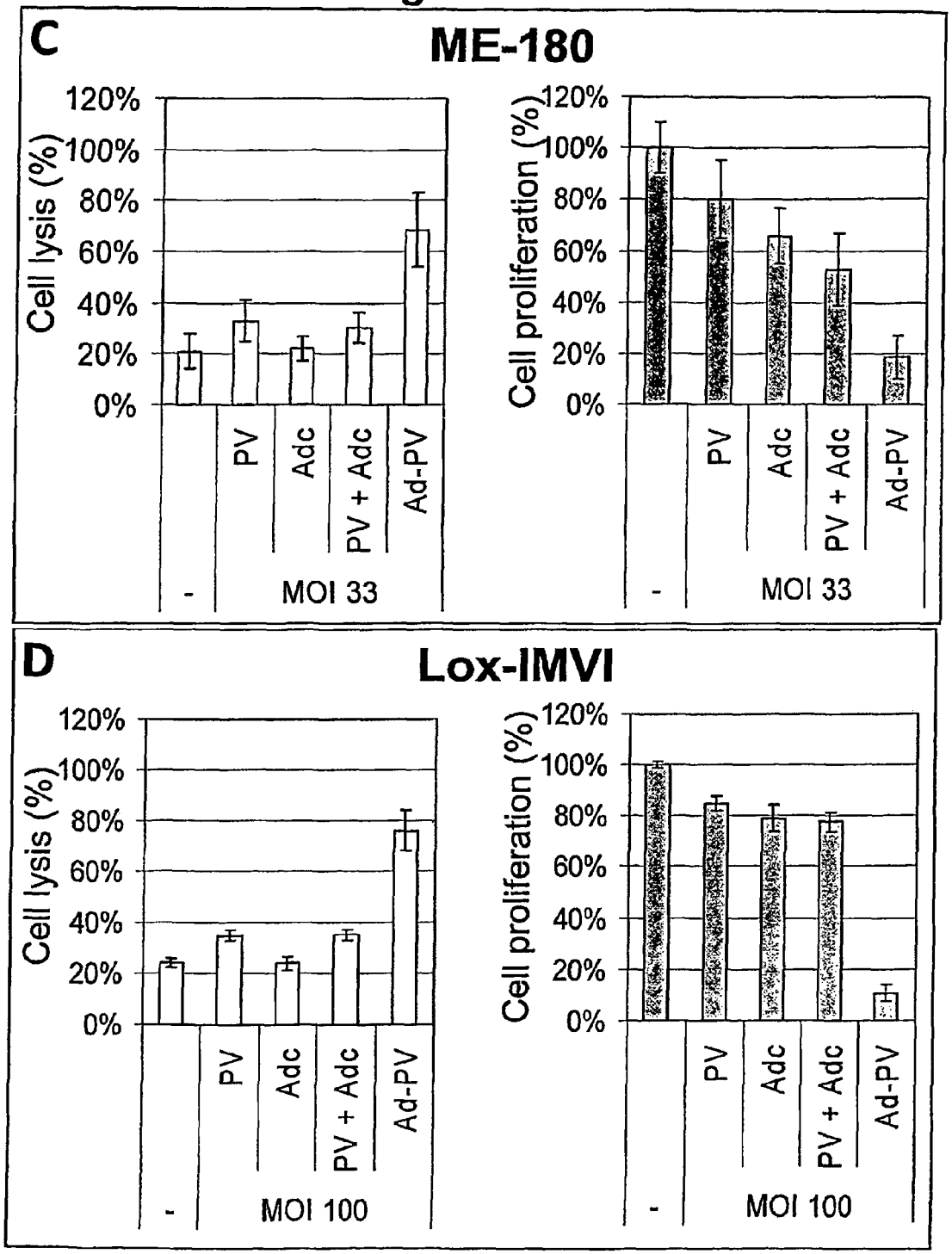
Figure 10:
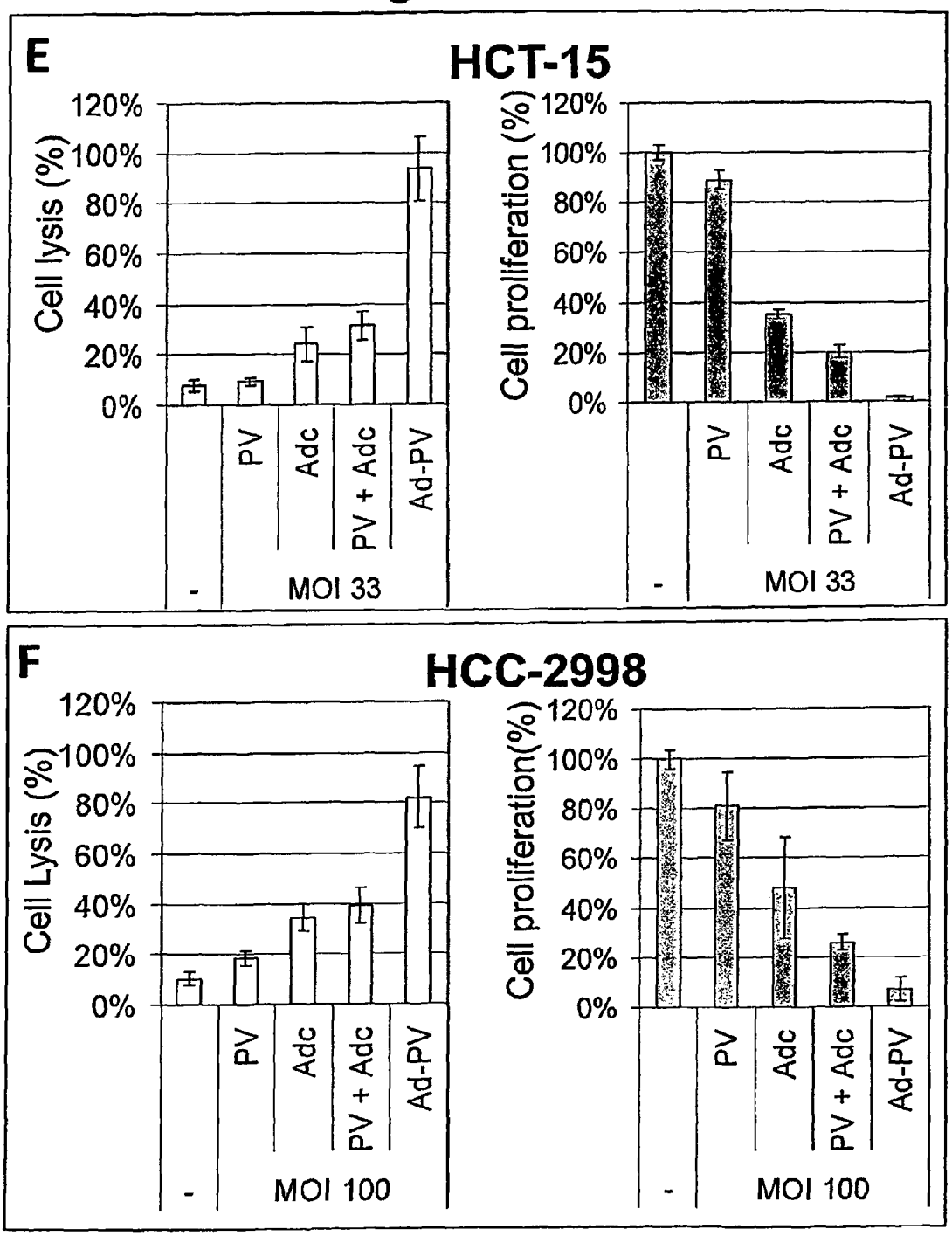
Figure 11:
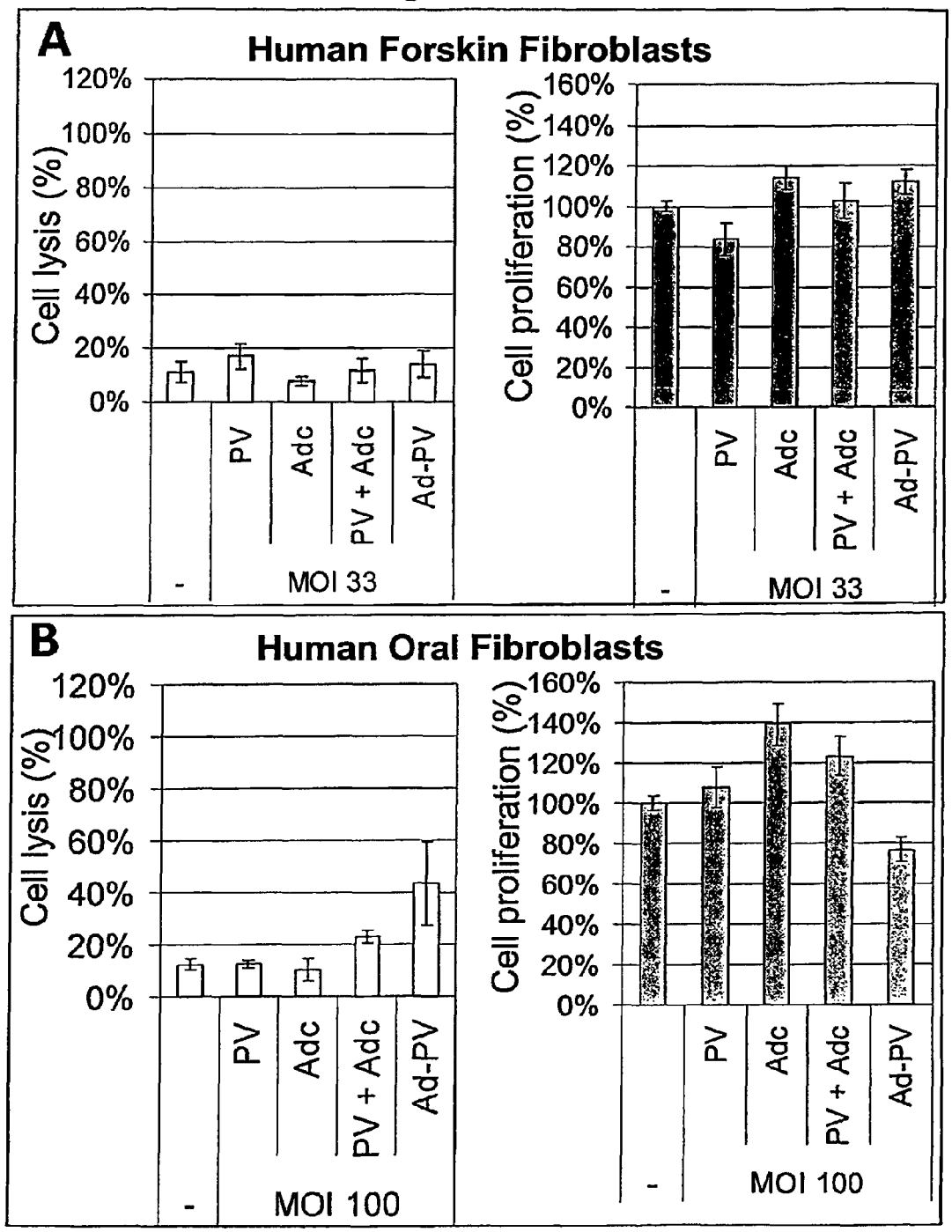
FIG. 11: Ad-hH-1-TO chimera has a limited cytotoxicity against_normal human primary cells. Human Foreskin fibroblasts (A), human oral fibroblasts (B), human melanocytes (C) and human astrocytes (D) were seeded in 96 well plates, and infected or not (−) with chimeric Ad-hH-1-TO (Ad-PV), Ad control (Adc), hH-1-TO parvovirus (PV) or a mixture of Ad control and hH-1-TO viruses (PV+Adc). After 5 days of incubation, cell lysis and cell proliferation were assessed by LDH and MTT assays, respectively.
Figure 11:
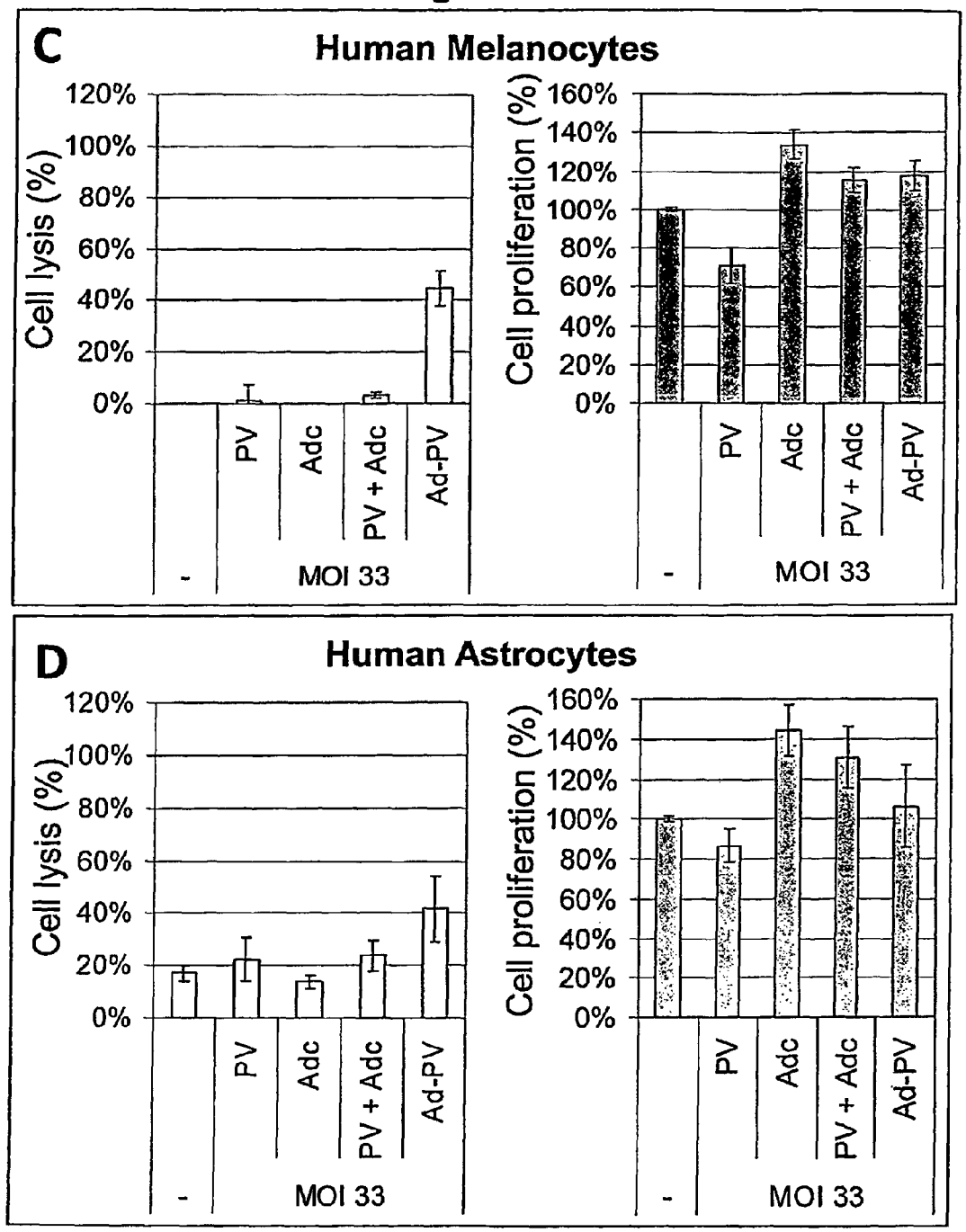

Here, the Ad-hH-1-TO chimera and both parental viruses (Ad control and hH-1-TO) were compared for their cytotoxic activities against a panel of human cancer and normal cell cultures by MTT (analysis of the cell proliferation) and LDH (analysis of the cell lysis) assays. The results obtained from these experiments are reported in Table 1 and FIGS. 10 and 11.

(PV), Ad control (Adc), combination of hH-1-TO and Ad control (PV+Adc) and Ad-hH-1-TO chimera (Ad-PV). Untreated cells were used as a control. Average values with relative standard deviations of a typical experiment performed in triplicate are shown.

In a first step, the cytotoxic activity of Ad-hH-1-TO chimera in HeLa cells known to be sensitive to hH-1-TO parvovirus infection was evaluated. In agreement with previous results hH-1-TO, used singly or in combination with Ad control, killed very efficiently HeLa cells. A more robust cytotoxic effect was observed with Ad-hH-1-TO, indicating that, under these experimental conditions, the PV cytostatic and cytotoxic potential is preserved or even enhanced once loaded into the Ad vector. As Ad control alone, displayed much weaker cytotoxic and cytostatic activities than those of hH-1-TO, it was concluded that the cytotoxicity of the chimeric Ad-hH-1-TO is mainly due to the PV component, in these cells (FIG. 10A).

In a second step, it was tested whether the chimera may allow its PV component to kill tumour cells otherwise resistant to PV direct infection. To this end, experiments were conducted using five different cell lines that are resistant to parvovirus cytotoxicity and which derived from cervical (ME-180 and low-passage CxCa), melanoma (Lox-IMVI) and colon (HCT-15 and HCC-2998) malignancies.

Infections with Ad and hH-1-TO viruses (used singly or in combination) had little effect on the growth of these cells. This was in striking contrast with the Ad-hH-1-TO chimera which was much more toxic and efficiently killed all tumour cell lines analyzed, indicating that the chimera has improved oncolytic activities in respect to the parental viruses from which it originated (FIG. 10B-F).

In a third step, it was important to verify that the tumour-specificity of PV cytotoxicity was kept when the PV was delivered by the Ad vector. To this end the cytotoxicity of the chimera was compared with the one of parental viruses in human primary cells of different origins, namely normal foreskin fibrostasts, oral fibroblasts, melanocytes and astrocytes. Although the time of virus incubation, before processing the cells for MTT and LDH assays, was one day longer in primary cultures in respect to cancer cells (5 vs. 4 days), the chimera did not display the same potency in

TABLE 1

Cytotoxicity of Ad-hH-1-TO chimera against various human cancer and primary cells in vitro

| | | | Cellular proliferation (%) (MTT assay) | | | | Cellular toxicity (%) (LDH assay) | | | | |
|---|---|---|---|---|---|---|---|---|---|---|---|
| | | MOI | Untreated | PV | Adc | PV + Adc | Ad-PV | Untreated | PV | Adc | PV + Adc | Ad-PV |
| Cancer Cells | | | | | | | | | | | | |
| Cervical cancer | HeLa | 10 | 100 ± 10 | 25 ± 4 | 65 ± 7 | 11 ± 3 | 7 ± 2 | 13 ± 1 | 82 ± 3 | 20 ± 5 | 86 ± 6 | 98 ± 6 |
| | CxCa | 33 | 100 ± 9 | 91 ± 15 | 58 ± 12 | 48 ± 9 | 10 ± 2 | 9 ± 3 | 20 ± 3 | 41 ± 8 | 47 ± 11 | 107 ± 16 |
| | ME180 | 33 | 100 ± 10 | 80 ± 15 | 66 ± 11 | 53 ± 14 | 19 ± 8 | 21 ± 7 | 33 ± 8 | 22 ± 5 | 32 ± 6 | 69 ± 14 |
| Melanoma | Lox-IMVI | 100 | 100 ± 1 | 85 ± 3 | 79 ± 6 | 78 ± 4 | 11 ± 3 | 24 ± 2 | 35 ± 2 | 24 ± 3 | 35 ± 2 | 76 ± 8 |
| Colon Cancer | HCT-15 | 33 | 100 ± 3 | 89 ± 4 | 35 ± 2 | 20 ± 3 | 2 ± 1 | 7 ± 2 | 9 ± 1 | 27 ± 7 | 31 ± 5 | 94 ± 13 |
| | HCC-2998 | 100 | 100 ± 4 | 81 ± 14 | 48 ± 20 | 26 ± 3 | 7 ± 5 | 10 ± 3 | 18 ± 3 | 34 ± 5 | 39 ± 7 | 82 ± 12 |
| Primary cells | | | | | | | | | | | | |
| Foreskin fibroblasts | | 33 | 100 ± 2 | 83 ± 8 | 114 ± 6 | 102 ± 9 | 112 ± 6 | 11 ± 4 | 17 ± 5 | 8 ± 2 | 12 ± 4 | 14 ± 5 |
| Oral fibroblasts | | 100 | 100 ± 4 | 108 ± 10 | 139 ± 11 | 123 ± 10 | 77 ± 6 | 12 ± 2 | 12 ± 2 | 10 ± 4 | 23 ± 3 | 43 ± 16 |
| Melanocytes | | 33 | 100 ± 1 | 71 ± 9 | 134 ± 7 | 115 ± 6 | 118 ± 8 | 3 ± 1 | 1 ± 6 | 2 ± 1 | 3 ± 1 | 45 ± 7 |
| Astrocytes | | 33 | 100 ± 1 | 87 ± 8 | 144 ± 13 | 131 ± 15 | 106 ± 20 | 17 ± 3 | 22 ± 8 | 14 ± 3 | 24 ± 6 | 42 ± 12 |

LDH and MTT results were performed after 4 (cancer cells) or 5 (normal cells) days of incubation with hH-1-TO killing normal cells that was previously reported against cancer cells. In particular, no cytotoxicity was found in human foreskin fibroblasts (FIG. 11A) while only minor cytotoxic effects were observed for the other primary cultures analyzed (FIG. 11B-D).

Figure 9:
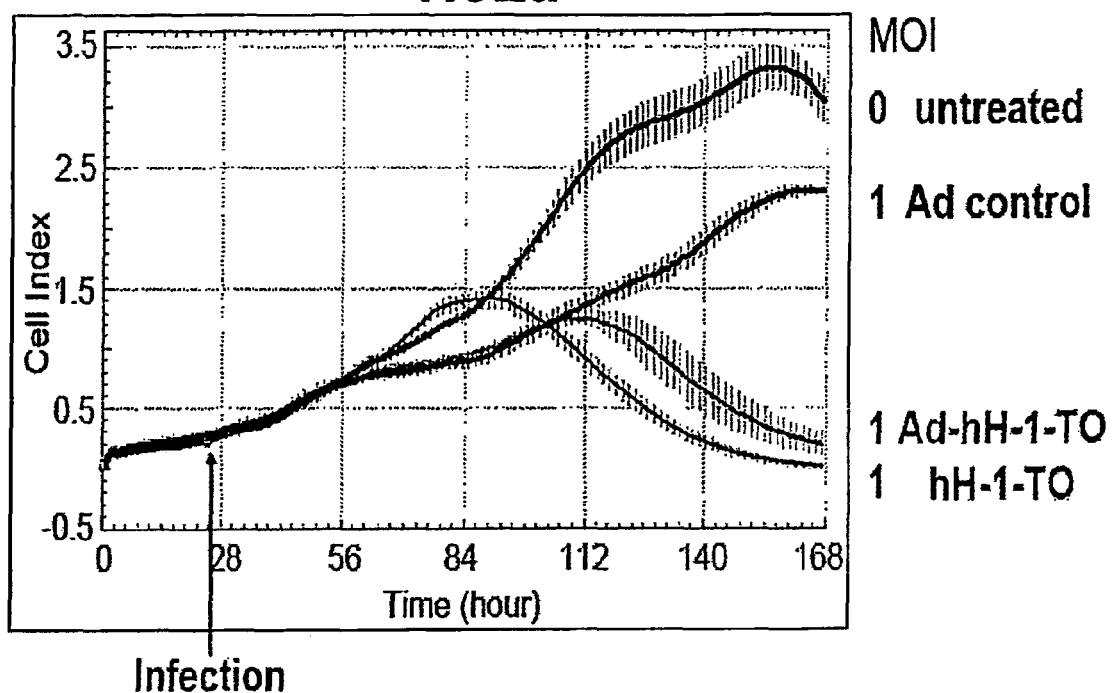
FIG. 9: Growth of human cancer cell lines infected with Ad-hH-1-TO, Ad control, hH-1-TO or the combination of Ad control and hH-1-TO viruses. HeLa (A), CxCa (B), ME-180 (C), Lox-IMVI (D), HCT-15 (E), HCC-2998 (F), and A549 (G), human cancer cells were seeded in 96 well E-plates (xCELLigence, Roche) and infected at the time indicated with Ad-hH-1-TO chimera, Ad control, hH-1-TO or the combination of Ad vector and hH-1-TO viruses. Untreated cells were used as control. Cell index values are proportional to cell numbers and were recorded and measured every 30 min for a maximum of 1 week using the xCELLigence System (Roche). Average values with relative standard deviations from a typical experiment performed in triplicate are shown.
Figure 9:
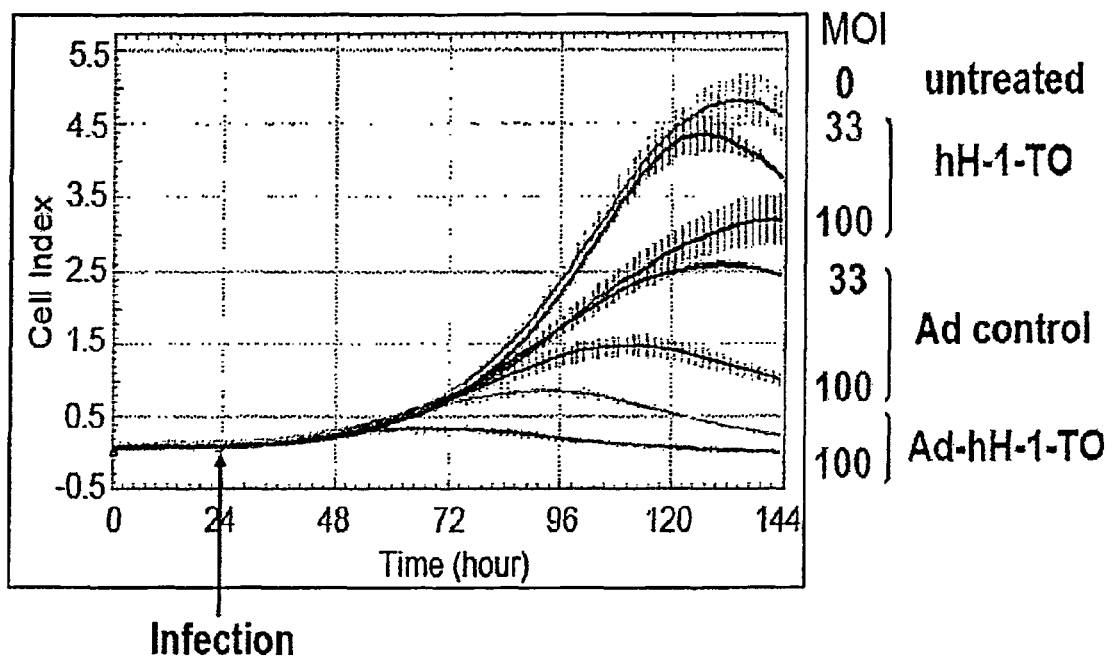
Figure 9:
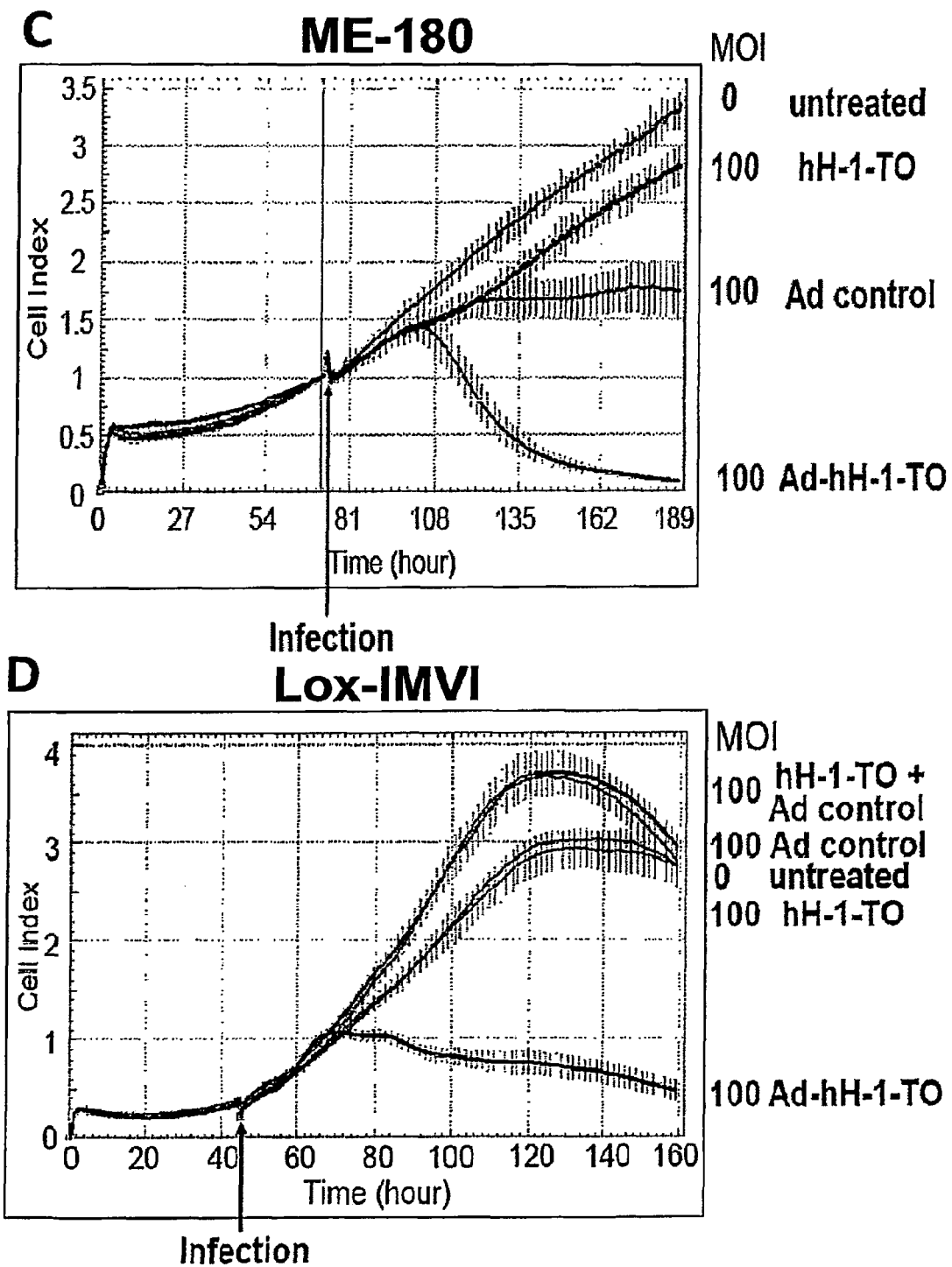
Figure 9:
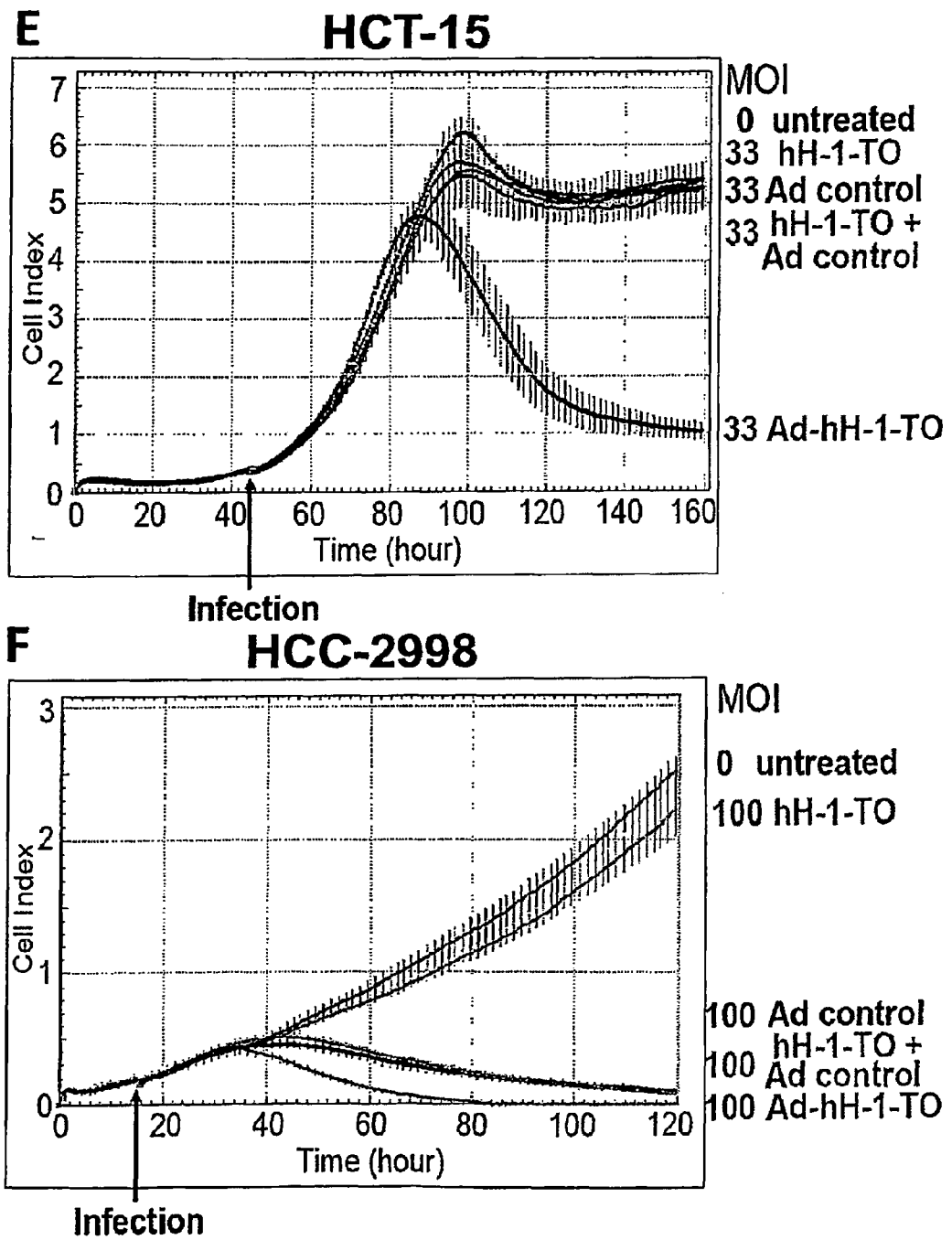
Figure 9:
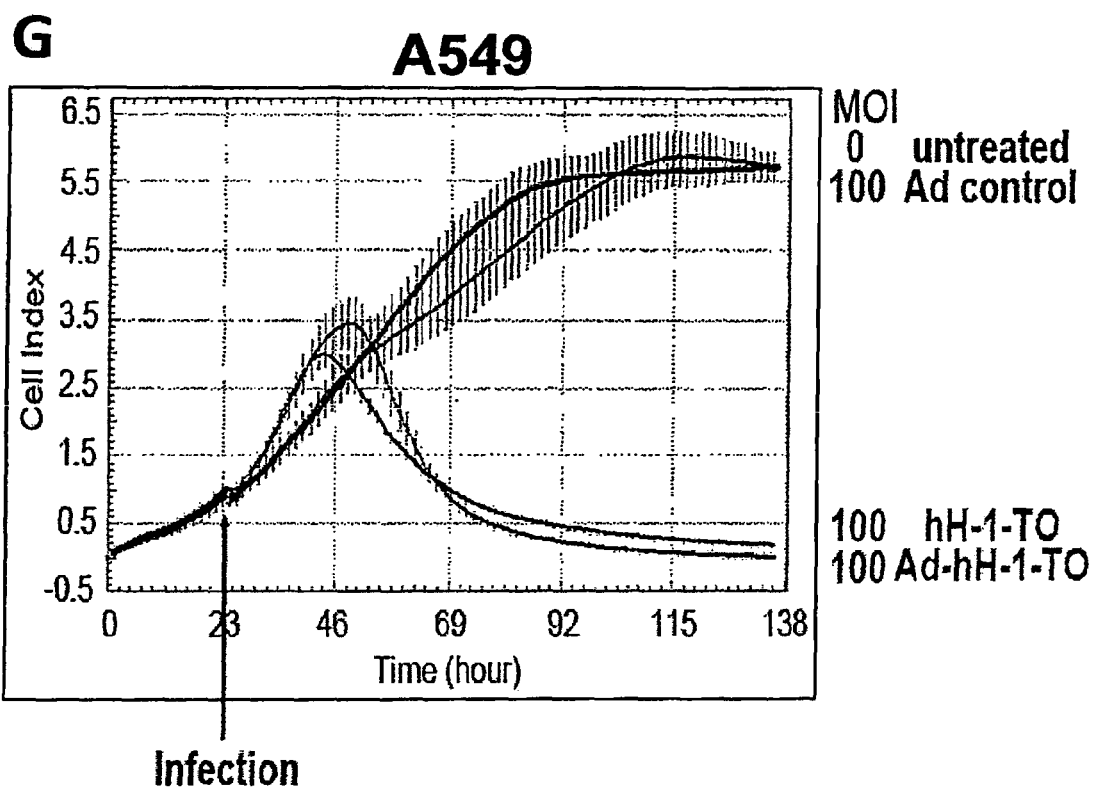

Next, the dynamic of tumour cell killing by Ad-hH-1-TO chimera and control viruses was further investigated using the xCELLigence system. With this device, it is possible to monitor in real time the proliferation and viability of the cells. The cancer cell lines previously analyzed by LDH and MTT assays with the addition of A549 lung carcinoma, were infected with Ad-hH-1-TO chimera and control viruses, and grown for further 5-7 days measuring the cell density every 30 min. FIG. 9 shows the growth curves of infected versus untreated cells. The Ad control virus had limited effect on the cellular growth of HeLa cells, while the parvovirus hH-1-TO was able to efficiently suppress the proliferation and induce death of nearly all cells. This striking killing ability was achieved to a similar extent when the parvovirus was delivered by the chimera (FIG. 9A). It is worth noting that the cytotoxic effect of the Ad-hH-1-TO chimera was delayed in comparison to the one induced by hH-1-TO (about 24 h) which could presumably be assigned to the time requested for PV rescue from the chimeric vector. In agreement with previous results (Table 1), CxCa, ME-180, Lox-IMVI, HCT-15 and HCC-2998 resulted quite resistant to hH-1-TO cytotoxicity with their growth curves being only very marginally affected by this virus (FIG. 9C-F). On the other hand, infection with Ad control induced strong cytotoxic effects only in colon cancer derived HCC-2998 (FIG. 9G), cytostatic effects in cervical carcinoma derived CxCa (FIG. 9B) and ME-180 (FIG. 9C) (for the former only when the virus was used at the high concentration of MOI 100), and no cytotoxicity at all in melanoma Lox-IMVI (FIG. 9D) and colon cancer HCT-15 (FIG. 9E). These results did not change when Ad control was sub-administered together with hH-1-TO. On the contrary, as previously observed in LDH and MTT assays, the Ad-hH-1-TO chimera was much more toxic compared with all infection controls. This virus efficiently killed all the cell lines tested, inducing strong cytotoxic effects already after 20-40 hours from infection (FIG. 9B-F). xCELLigence growth-monitoring of lung cancer derived A549 showed that similarly to HeLa cells. This cell line resulted sensitive to both hH-1-TO and chimeric Ad-hH-1-TO cytotoxicity (FIG. 9G), confirming that the oncolytic potential of the chimera is preserved in cancer cell lines originally permissive to parvovirus. Altogether, these results highlight the improved oncolytic activity of the Ad-hH-1TO chimera.

Example 6

Enhanced Oncotoxic Potential of the Ad-PV Chimera

It is known that H-1PV induces cytopathic effects on a large number of cancer cells [10]. However, there are also cancer cell lines which are weakly susceptible or completely refractory to H-1PV cytotoxicity. Experiments of the inventors showed that the hH-1 and hH-1-TO parvoviruses exerted similar cytotoxic activities against HeLa cells as measured by LDH assay, indicating that the modification introduced into the P4 promoter region did not modify the oncolytic activity of the parvovirus.

The cytotoxic activities of the Ad-hH-1-TO (Ad-PV) chimera and both parental viruses [Ad control (Adc) and hH-1-TO (PV)] were compared against a panel of human cancer cell lines differing in their sensitivity to H-1PV infection including highly sensitive cells (cervical carcinoma-derived HeLa, melanoma pMelL), poorly sensitive cells (lung cancer-derived A549) and resistant cells (cervical carcinoma-derived ME-180, melanoma Lox-IMVI, colon cancer HCT-15 and HCC-2998).

Figure 13:
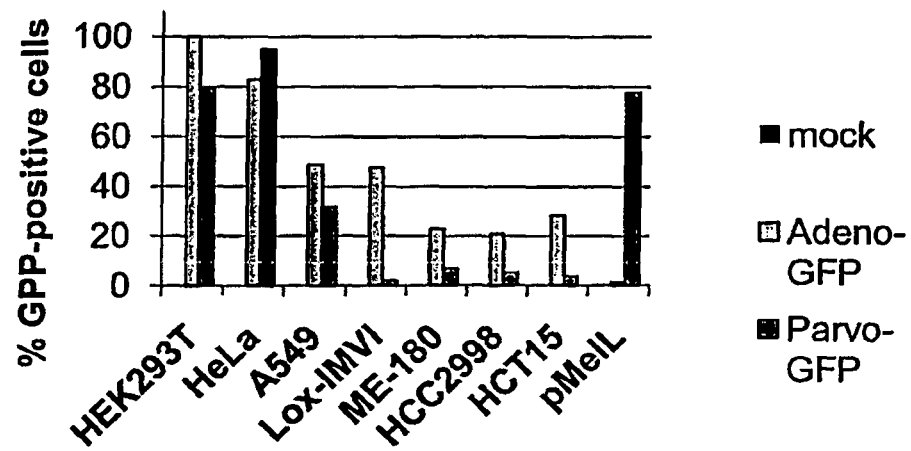
FIG. 13: Transduction efficiency of recombinant Ad-GFP and H-1GFP. The indicated cells were infected with recombinant Ad or PV (10 TU/cell as quantified by using HEK-293T cells) carrying the GFP reporter gene. After 48 and 72 h cells were harvested and analyzed by flow cytometry. Values represent the percentage of GFP positive cells.
Figure 13:
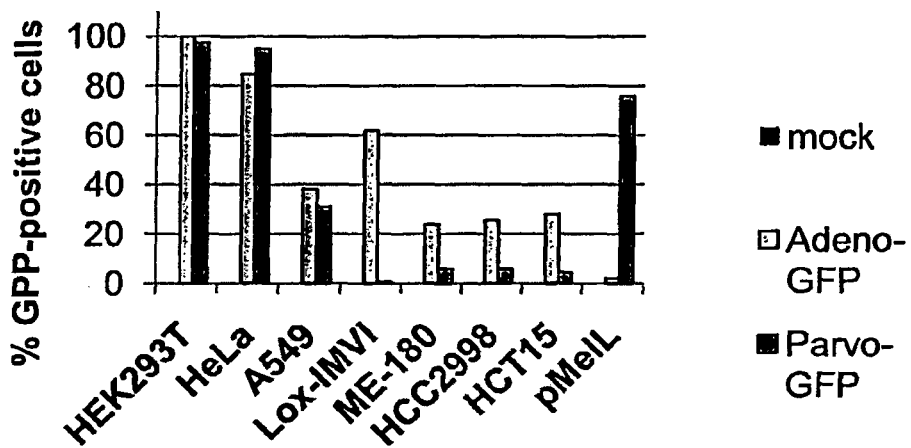

In a first step, the susceptibility of these cells to infection with Ad5 and H-1PV was determined by using recombinant viruses harboring the GFP reporter gene (Ad-GFP or H-1-GFP). As illustrated in FIG. 13, FACS analysis performed 48 and 72 h after infection revealed that Ad-GFP and H-1-GFP transduced HeLa and A549 in a similar manner, while Ad-GFP was much more efficient than H-1GFP in transducing the cell lines previously identified as resistant to H-1PV cytotoxicity. As expected pMelL cells (which lack the Ad receptors on their surface), were efficiently transduced by H-1GFP but not Ad-GFP (FIG. 13).

In a second step, viral cytotoxicity was evaluated by MTT assay (analysis of cell viability), LDH assay (analysis of cell lysis) and XCellIgence (real time analysis of cell growth).

(i) The cytotoxic activity of the Ad-PV chimera was first evaluated in HeLa cells, in comparison with that of the parental viruses (FIG. 14A). Cells were infected with equal amounts of the different viruses. In agreement with previous results, LDH and MTT assays revealed that PV used singly or in combination with the Ad control, killed HeLa cells very efficiently. A similar cytotoxic effect was observed with the Ad-PV chimera indicating that, under these experimental conditions, the PV cytotoxic potential is preserved upon PV delivery through the Ad vector. As the Adc alone was much less toxic than PV, the inventors concluded that the cytotoxicity of the chimeric Ad-PV in these cells was mainly due to the PV component (FIG. 14A). In agreement with these results, analysis of the cell growth curves using the XCellIgence system, showed that the Adc virus had limited effect on the proliferation of HeLa cells, while the PV was able to efficiently suppress the proliferation and induce death of these cells (FIG. 14B). This striking HeLa cell growth suppression and killing were achieved to a similar extent when the PV was delivered by the chimera. It is worth noting that the cytotoxic effect of the Ad-PV chimera was delayed by approximately 24 h in comparison to the one induced by PV which would be consistent with the time needed for PV rescue from the chimeric vector in these cells. A549 cells were also found to be sensitive to both PV and chimeric Ad-PV cytotoxicity, confirming that the oncolytic potential of H-1PV is kept by the chimeric virus (FIGS. 14C and D). In keeping with the fact that A549 are less susceptible to H-1PV infection than HeLa cells, a ten times higher concentration of PV or Ad-PV chimera was required in order to efficiently kill these cells.

Figure 14:
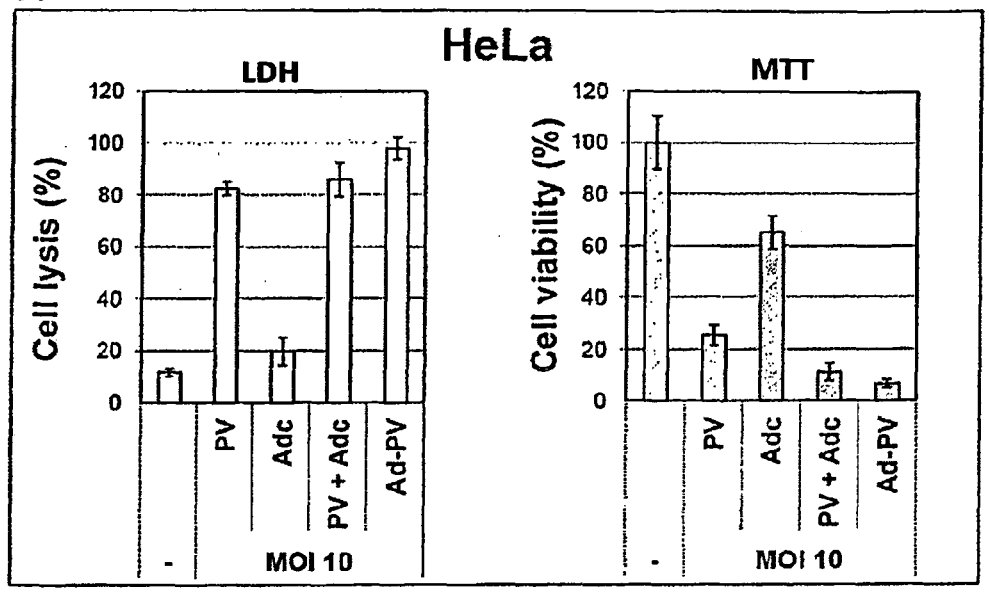
FIG. 14: Improved cytotoxic activity of Ad-hH-1-TO chimera_cancer cell lines. HeLa (A and B), A-549 (C and D), ME-180 (E and F), Lox-IMVI (G and H), HCT-15 (I and J), HCT 2998 (K and L) and pMelL (M and N) human cancer cells were seeded in 96 well (LDH and MTT assays) or 96 well E-plates (xCELLigence, Roche) and infected with the indicated MOI of Ad-hH-1-TO chimera (Ad-PV), Ad control (Adc), hH-1-TO (PV) or the combination of Ad vector and hH-1-TO (PV+Adc) viruses. Untreated cells (−) were used as control. Values showed in panels A, C, E, G, I, K and M represent the percentage of lysed (LDH assay) or viable (MTT) cells calculated as described in the materials and methods section. Panels B, D, F and H, J, L, and N show the proliferation curves of the cells infected or not with viruses measured in real time using the XCelligence system. Cell index values are proportional to cell numbers and were recorded and measured every 30 min for a maximum of 1 week. Results are presented as average values with relative standard deviation bars from triplicate measurements in a typical experiment. Arrows indicate the time of infection.
Figure 14:
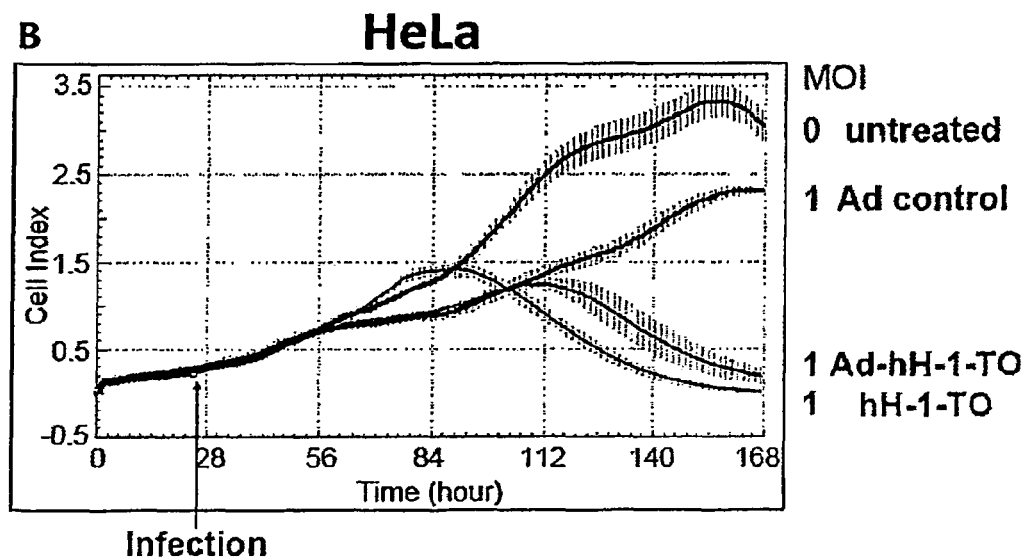
Figure 14:
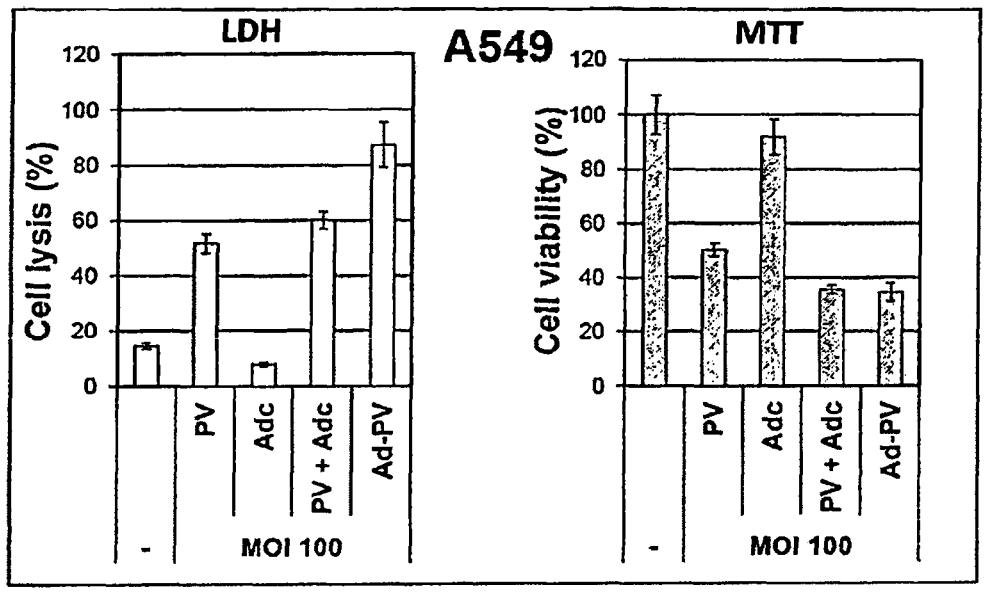
Figure 14:
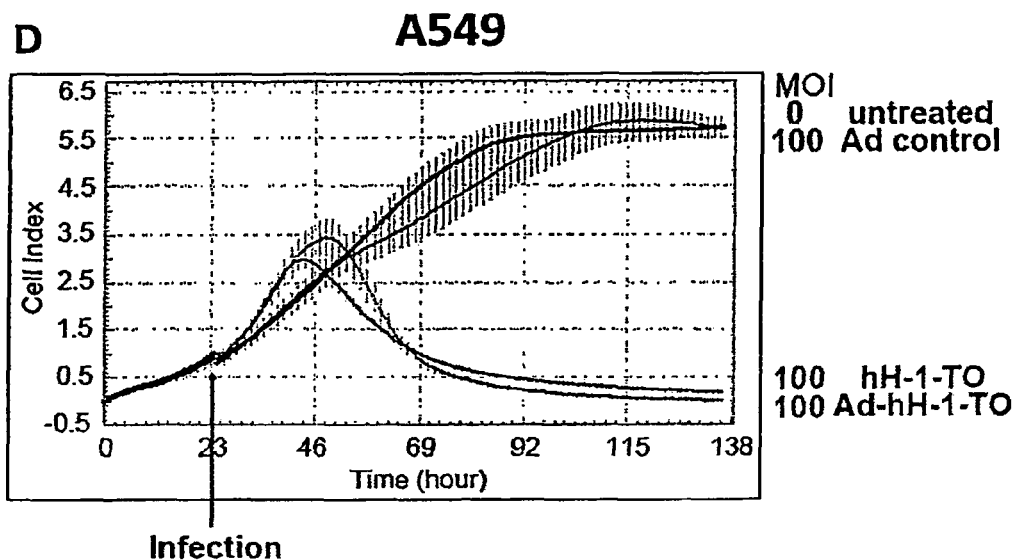
Figure 14:
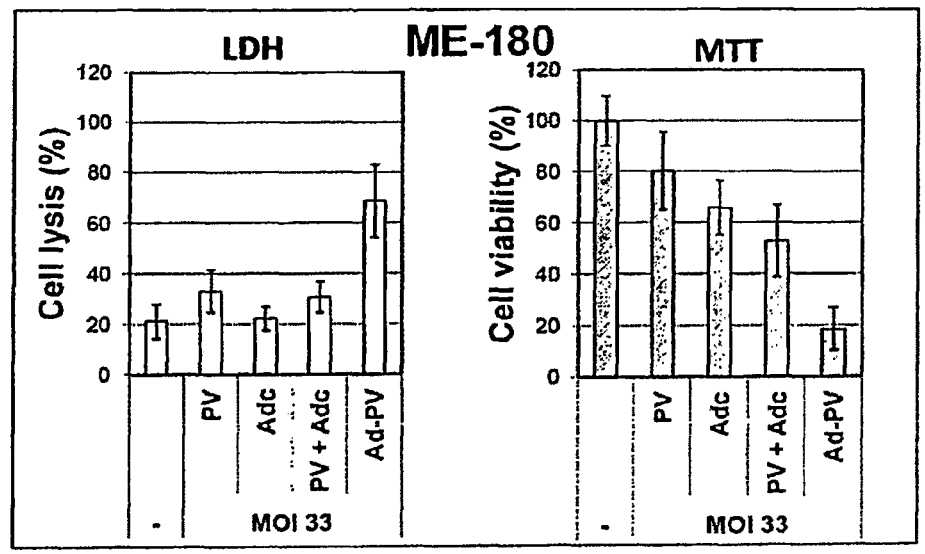
Figure 14:
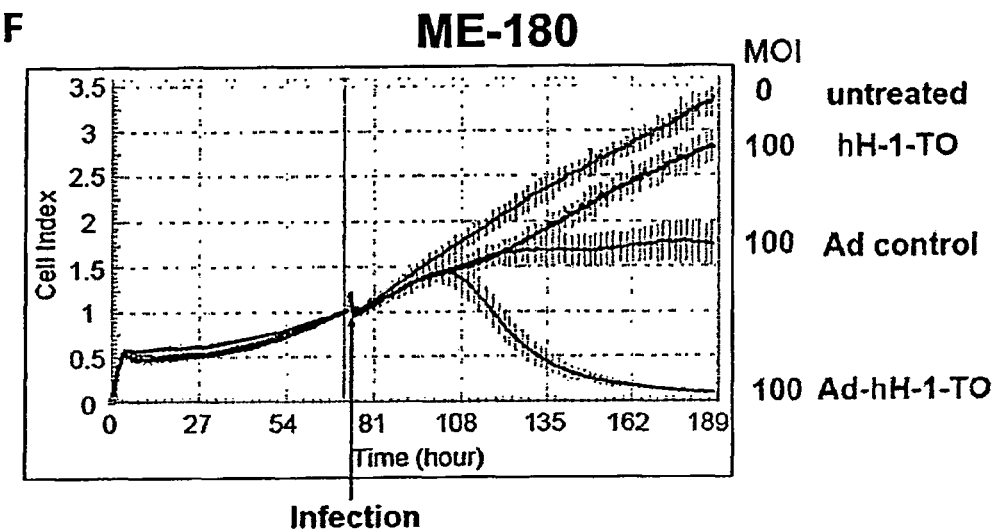
Figure 14:
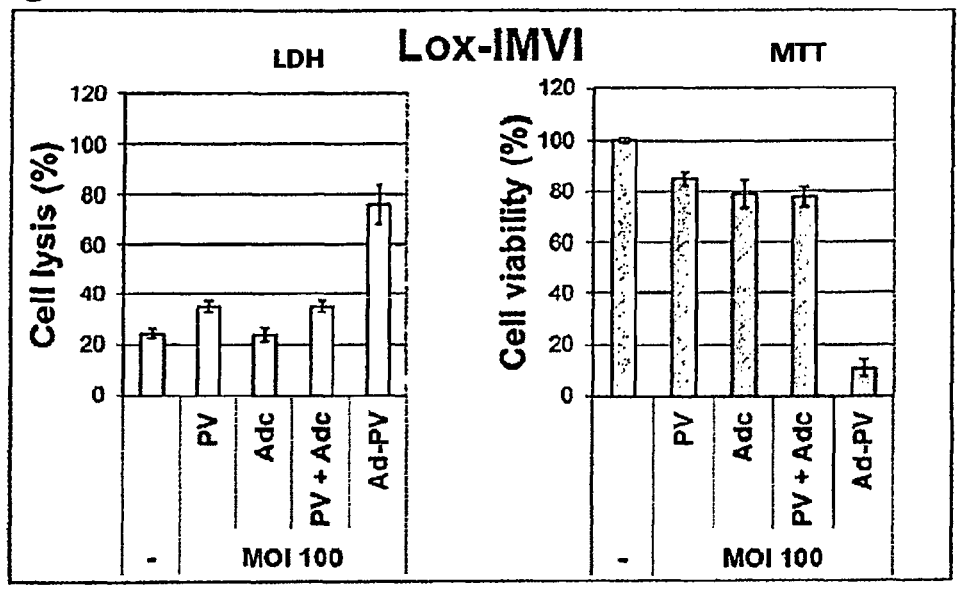
Figure 14:
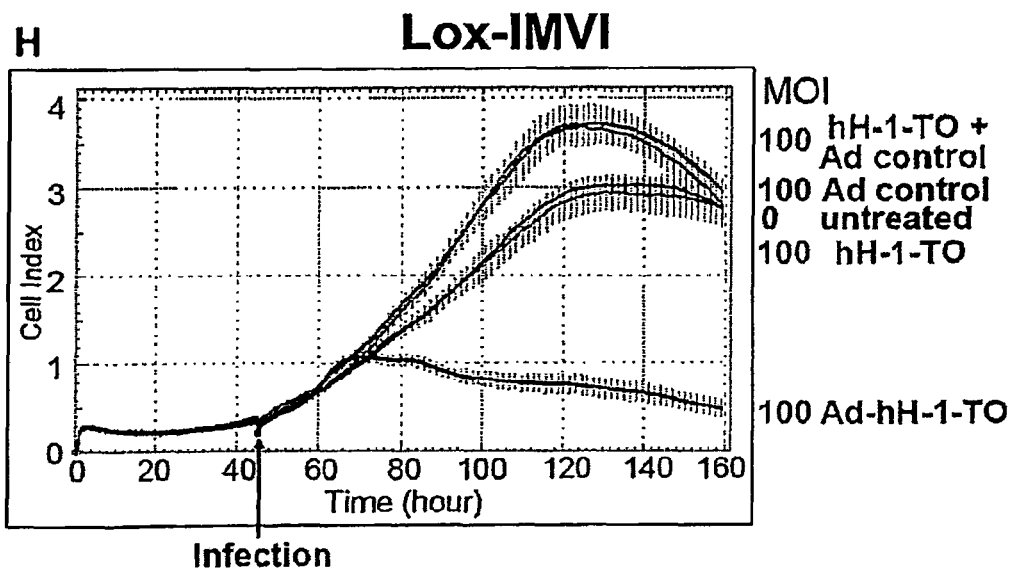
Figure 14:
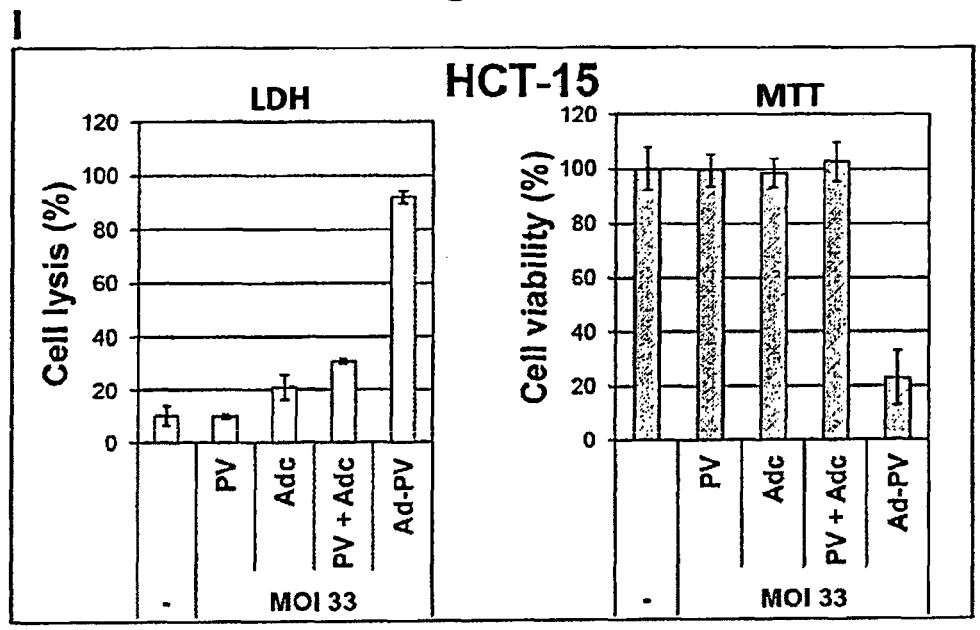
Figure 14:
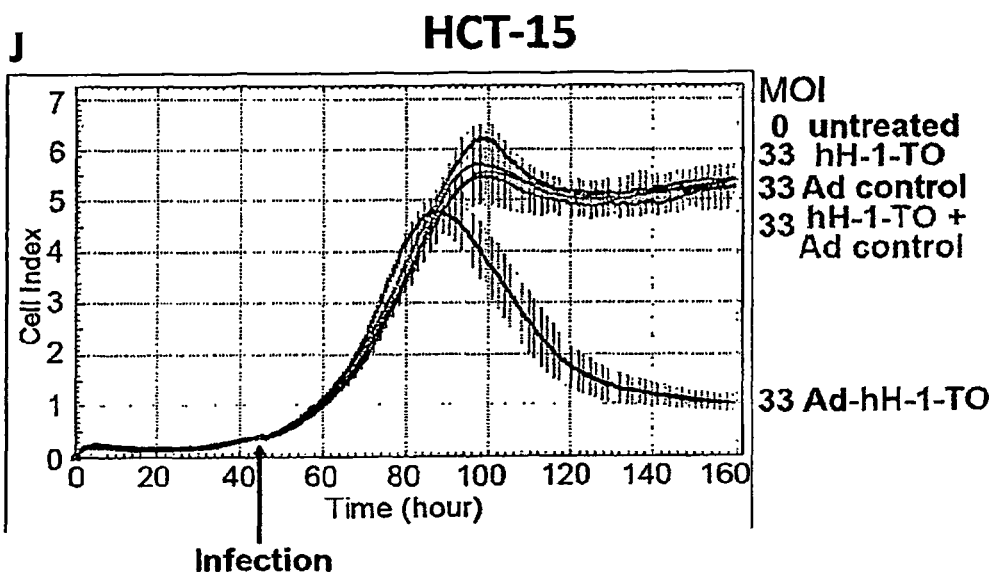
Figure 14:
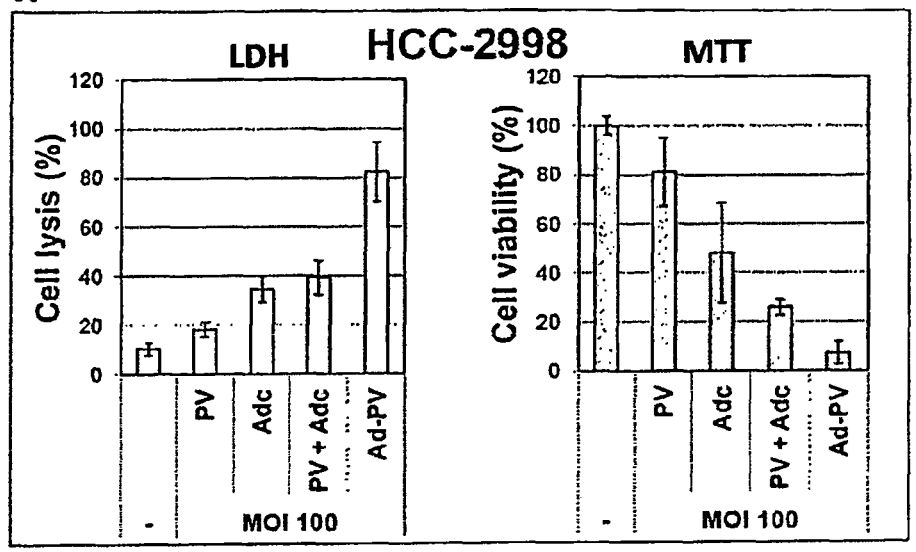
Figure 14:
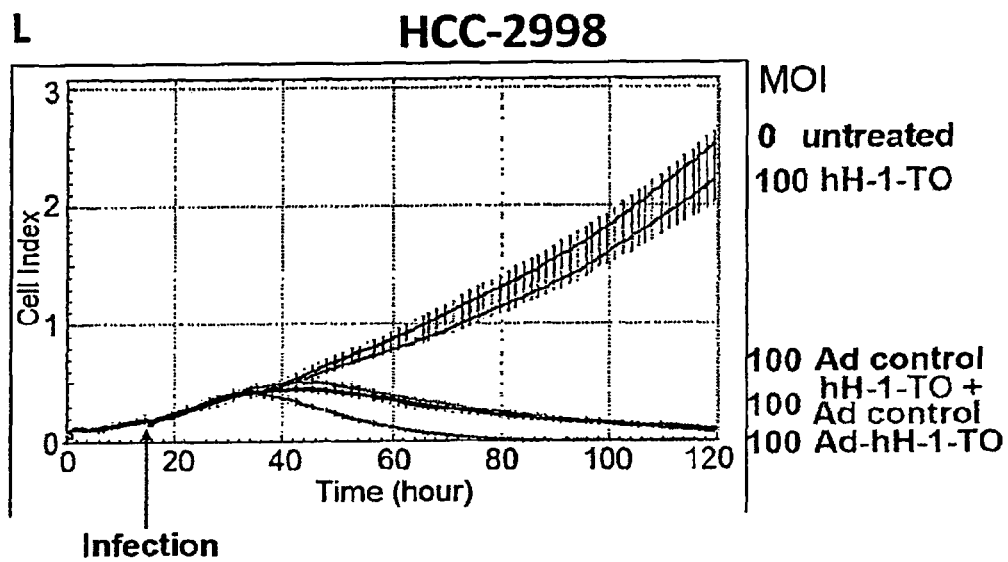
Figure 14:
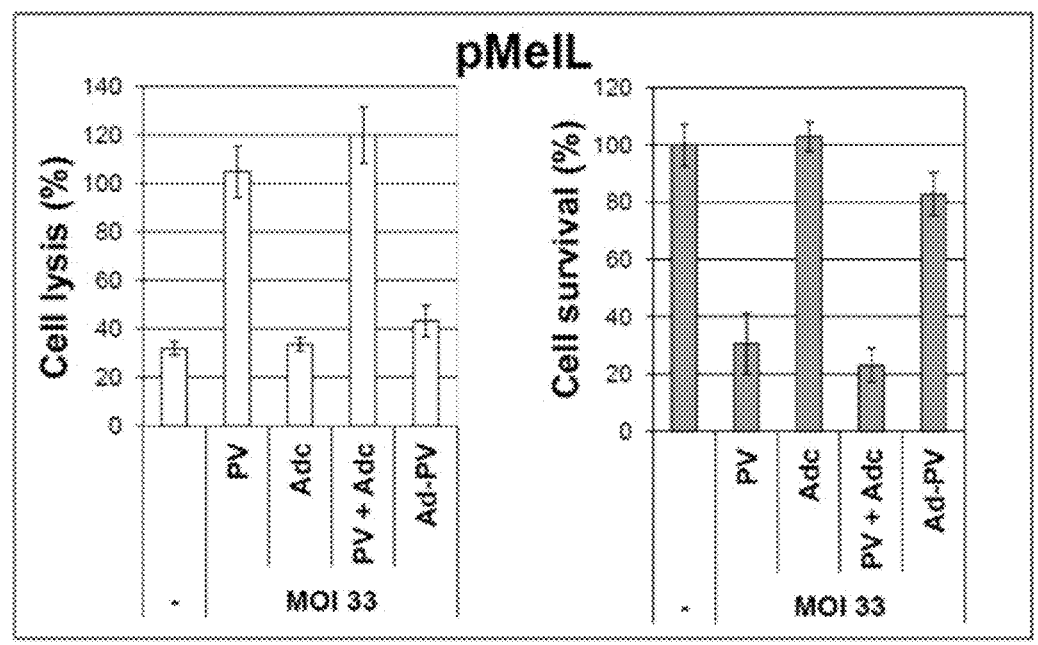
Figure 14:
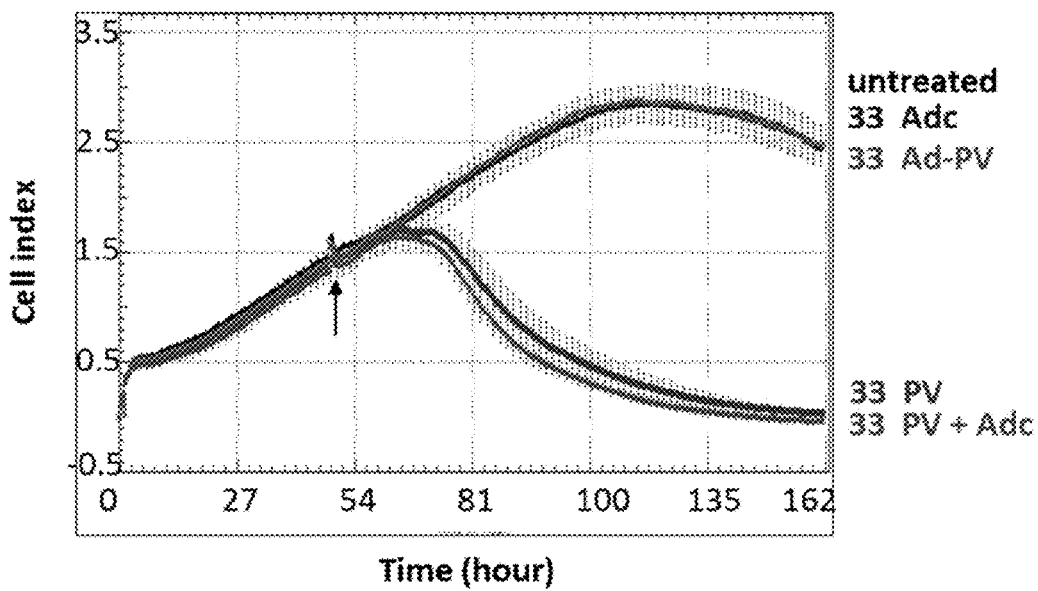

(ii) The inventors then tested whether the chimera is able to kill tumour cells previously identified as being resistant to direct H-1PV infection, namely ME-180, Lox-IMVI, HCT-15 and HCC-2998 (FIG. 14). MTT and LDH assays showed that infections with Ad and PV viruses (used singly or in combination) had little cytotoxic effects on these cells. In striking contrast, the Ad-PV chimera was much more toxic and efficiently killed all tumour cell lines analyzed, indicating that the chimera has an improved oncolytic activity as compared to the parental viruses from which it originated (FIGS. 14E, G, I and K). Kinetic analyses showed that the growth of above cell lines was only marginally disturbed by PV, confirming their significant resistance to the parvoviruses (FIGS. 14F, H, J and L). On the other hand, the Adc virus had varying toxic effects in these cells, ranging from full growth suppression (HCC-2998: see FIG. 14L) or growth retardation (ME-180: see FIG. 14F), to full resistance (Lox-IMVI and HCT-15: see FIGS. 14H and J, respectively). Similar results were obtained with the Adc was used in combination with PV. Interestingly, the Ad-PV chimera was found to be much more toxic than either parental viruses, fully suppressing the growth of all cells and inducing strong cytotoxic effects already at 20-40 hours post infection (FIGS. 14F, H, J and L).

(iii) As a control, the Ad-5 receptor-null pMelL cell line (30) was also included in this analysis. As shown in FIGS. 14M and N, these cells were sensitive to PV cytotoxicity, but completely resistant to both the Adc and Ad-PV chimera, indicating the chimera exerts its cytotoxicy only in cells competent for Ad uptake (FIGS. 14M and N).

Figure 15:
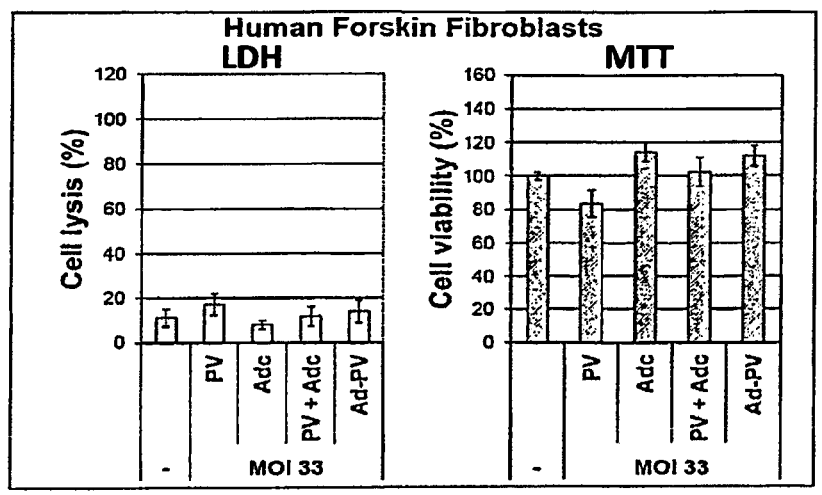
FIG. 15: Limited cytotoxicity of the Ad-hH-1-TO chimera for normal human primary cells. Human foreskin fibroblasts (A), oral fibroblasts (B), melanocytes (C) and astrocytes (D) were seeded in 96 well plates, and infected or not (−) with chimeric Ad-hH-1-TO (Ad-PV), Ad control (Adc), hH-1-TO parvovirus (PV) or a mixture of Ad control and hH-1-TO viruses (PV+Adc). After 5 days of incubation, % of lysed or viable cells were assessed by LDH and MTT assays, respectively as described in materials and methods.
Figure 15:
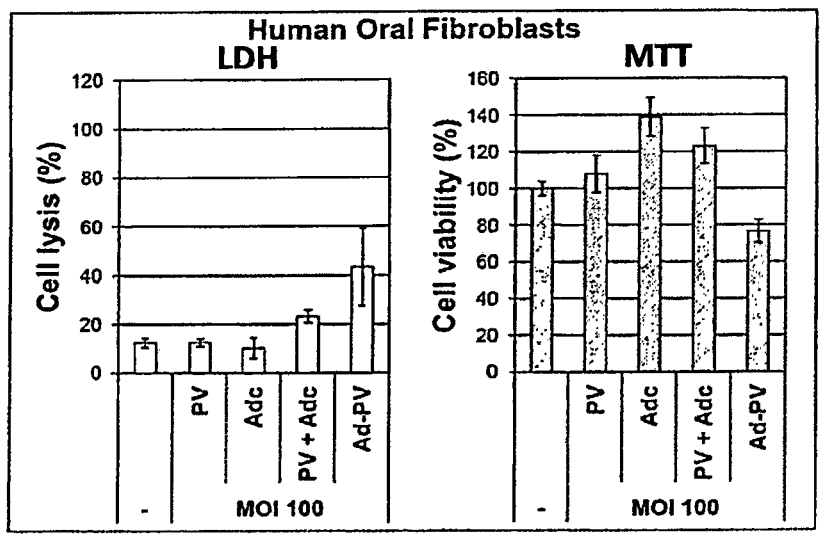
Figure 15:
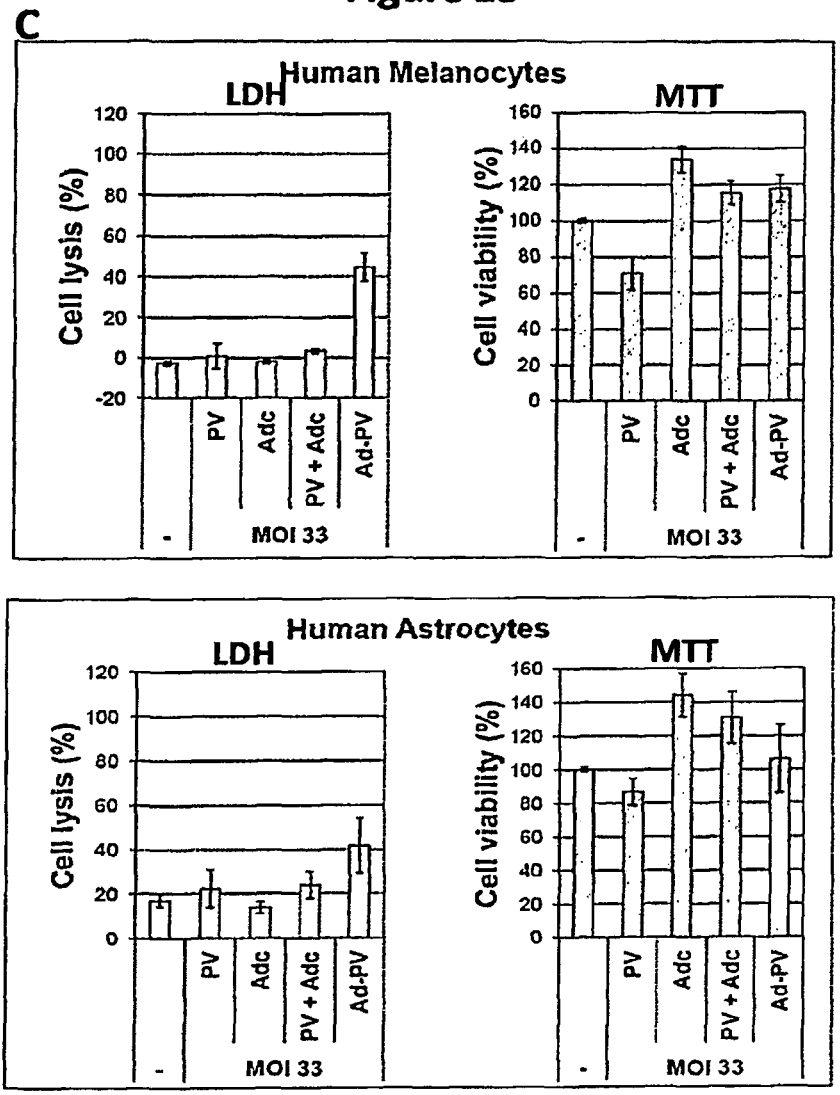
Figure 16:
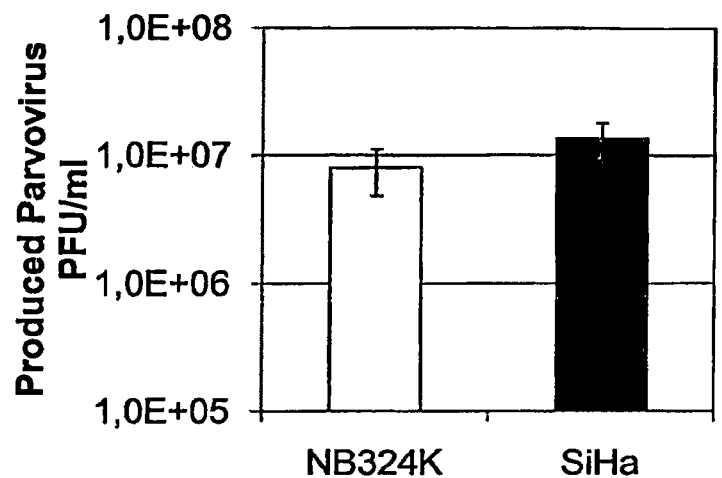
FIG. 16: Production, spreading and cytotoxicity of progeny parvoviruses in cells infected with the Ad-PV chimera. (A) Parvovirus production: NB324K or SiHa cells were infected with Ad-PV chimeras used at MOI 10 (NB324K) or 1 (SiHa) and culture media were renewed after 1 day to remove unbound viruses. After further incubation for 4 to 5 days, cells were harvested within their medium and lysed. Crude virus preparations were analyzed for the presence of parvoviruses by plaque assay. Titres of produced parvovirus are expressed in PFU/ml. (B) Parvovirus production and spreading: NB324K cells were infected with equivalent genomic amounts of Ad-PV chimera or H-1PV wild type virus (input, 10 Vg/seeded cell). After 96 h, cells were collected in their medium and subjected to three freeze-thaw cycles. After treatment with 50 U/ml of Benzonase for digesting cellular DNA and nonencapsidated viral DNA, crude cell extracts were analyzed for their content of full viral particles by qRT-PCR, as described in Materials and Methods. (C) Parvovirus spreading: HeLa cells were infected with Ad-PV chimeras (25 Vg/cell). At 10 h post-infection, one set of dishes was treated with 0.1 U/ml of neuraminidase (+NA) in order to prevent second rounds of parvovirus infection, while another set was left untreated (−NA). Benzonase pre-treated total cell lysates were analyzed by qRT-PCR for virus particle contents. (D) Parvovirus spreading and cytotoxicity: HeLa cells, grown in 96 wells plates, were infected with Ad-PV chimeras, treated or not with NA as described in panel C, and processed for LDH assay after 72 h.
Figure 16:
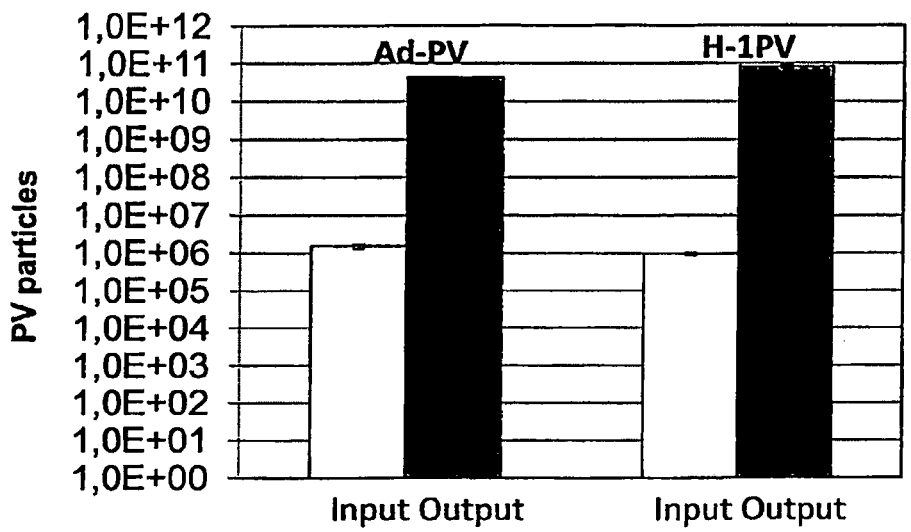
Figure 16:
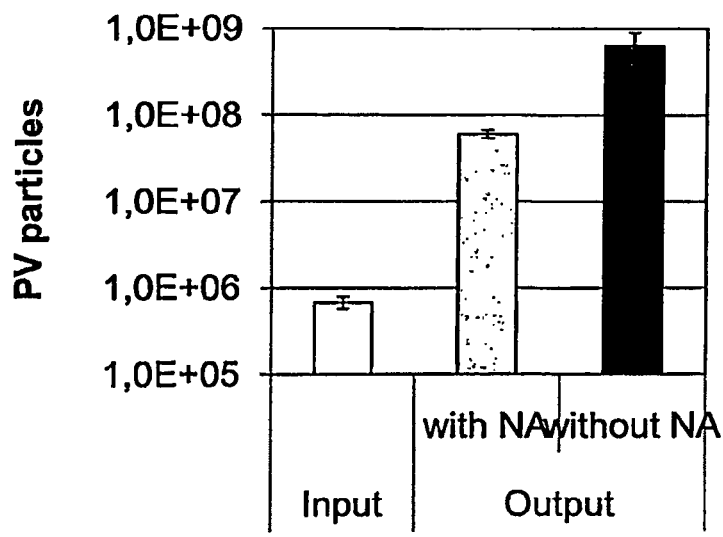
Figure 16:
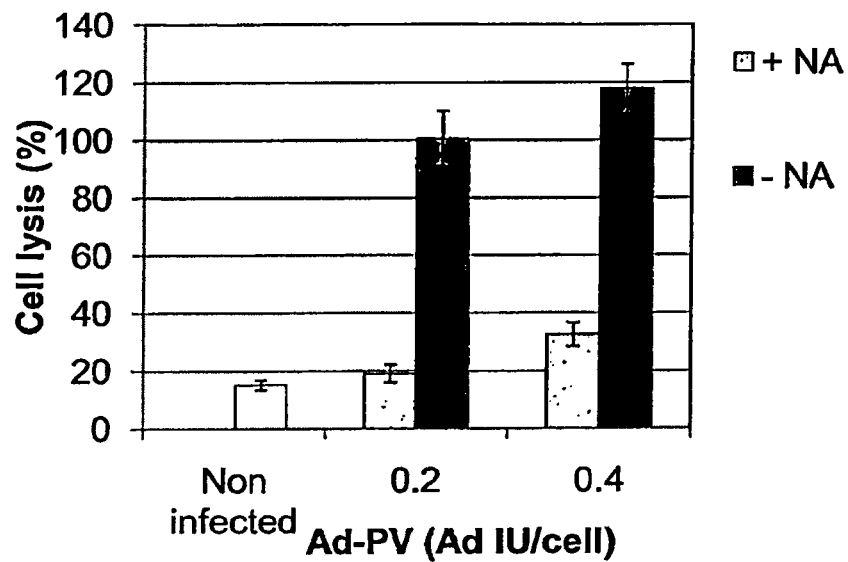

In a third step, it was important to verify that the tumour-specificity of PV cytotoxicity was kept when the PV was delivered by the Ad vector. To this end, the cytotoxicity of the chimera was compared with that of its parental viruses in human primary cells of different origins, namely normal foreskin fibroblasts, oral fibroblasts, melanocytes and astrocytes using LDH and MTT assays. Even after a longer virus incubation compared with cancer cells (5 vs. 4 days), normal cells were found to be fully resistant (foreskin fibroblsts) or only little sensitive (oral fibroblasts, melanocytes and astrocytes) to the cytotoxic activity of the Ad-PV chimera in striking contrast with the above mentioned high sensitivity of cancer cells (FIGS. 15 A-D).

Altogether, these results show the improved oncolytic activity of the Ad-PV chimera compared with Ad and PV parental viruses.

LIST OF REFERENCES

1. Russell, W. C., *Adenoviruses: update on structure and function*. J Gen Virol, 2009. 90(Pt 1): p. 1-20.
2. Edelstein, M. L., et al., *Gene therapy clinical trials worldwide 1989-2004—an overview*. J Gene Med, 2004. 6(6): p. 597-602.
3. Kurreck, J., Antisense technologies. *Improvement through novel chemical modifications*. Eur J Biochem, 2003. 270 (8): p. 1628-44.
4. Mathis, J. M., M. A. Stoff-Khalili, and D. T. Curiel, *Oncolytic adenoviruses—selective retargeting to tumor cells*. Oncogene, 2005. 24(52): p. 7775-91.
5. Everts, M. and D. T. Curiel, *Transductional targeting of adenoviral cancer gene therapy*. Curr Gene Ther, 2004. 4(3): p. 337-46.
6. Rein, D. T., M. Breidenbach, and D. T. Curiel, *Current developments in adenovirus-based cancer gene therapy*. Future Oncol, 2006. 2(1): p. 137-43.
7. Peng, Z., *Current status of gendicine in China: recombinant human Ad-p53 agent for treatment of cancers*. Hum Gene Ther, 2005. 16(9): p. 1016-27.
8. Liu, T. C., E. Galanis, and D. Kim, *Clinical trial results with oncolytic virotherapy: a century of promise, a decade of progress*. Nat Clin Pract Oncol, 2007. 4(2): p. 101-17.
9. Rommelaere, J. and J. J. Cornelis, *Antineoplastic activity of parvoviruses*. J Virol Methods, 1991. 33(3): p. 233-51.
10. Rommelaere, J., et al., *Oncolytic parvoviruses as cancer therapeutics*. Cytokine Growth Factor Rev. 21(2-3): p. 185-95.
11. Cornelis, J. J., et al., *Parvovirus oncosuppression*, in *Parvoviruses*, J. R. Kerr, Cotmore, S. F., Bloom, M. E., Linden, R. M., Parrish, C. R. (Eds.), Editor. 2006, Hodder Arnold: London. p. 365-378.
12. Grekova, S., et al., *Activation of an antiviral response in normal but not transformed mouse cells: a new determinant of minute virus of mice oncotropism*. J Virol. 84(1): p. 516-31.
13. Hristov, G., et al., *Through Its Nonstructural Protein NS1, Parvovirus H-1 Induces Apoptosis via Accumulation of Reactive Oxygen Species*. J Virol, 2010. 84(12): p. 5909-22.
14. Ran, Z., et al., *Parvovirus H-1-induced cell death: influence of intracellular NAD consumption on the regulation of necrosis and apoptosis*. Virus Res, 1999. 65(2): p. 161-74.
15. Ohshima, T., et al., *Induction of apoptosis in vitro and in vivo by H-1 parvovirus infection*. J Gen Virol, 1998. 79 (Pt 12): p. 3067-71.
16. Di Piazza, M., et al., *Cytosolic activation of cathepsins mediates parvovirus H-1-induced killing of cisplatin and TRAIL-resistant glioma cells*. J Virol, 2007. 81(8): p. 4186-98.
17. Jackson, D. A., R. H. Symons, and P. Berg, *Biochemical method for inserting new genetic information into DNA of Simian Virus 40: circular SV40 DNA molecules containing lambda phage genes and the galactose operon of Escherichia coli*. Proc Natl Acad Sci USA, 1972. 69(10): p. 2904-9.
18. Mathenge, E. G., et al., *Fusion PCR generated Japanese encephalitis virus/dengue 4 virus chimera exhibits lack of neuroinvasiveness, attenuated neurovirulence, and a dual-flavi immune response in mice*. J Gen Virol, 2004. 85(Pt 9): p. 2503-13.
19. Gluzman, Y. and K. Van Doren, *Palindromic adenovirus type 5-simian virus 40 hybrid*. J Virol, 1983. 45(1): p. 91-103.
20. Fisher, K. J., et al., *A novel adenovirus-adeno-associated virus hybrid vector that displays efficient rescue and delivery of the AAV genome*. Hum Gene Ther, 1996. 7(17): p. 2079-87.
21. Caplen, N. J., et al., *Adeno-retroviral chimeric viruses as in vivo transducing agents*. Gene Ther, 1999. 6(3): p. 454-9.
22. Lieber, A., et al., *Integrating adenovirus-adeno-associated virus hybrid vectors devoid of all viral genes*. J Virol, 1999. 73(11): p. 9314-24.
23. Tan, B. T., L. Wu, and A. J. Berk, *An adenovirus-Epstein-Barr virus hybrid vector that stably transforms cultured cells with high efficiency*. J Virol, 1999. 73(9): p. 7582-9.
24. Goncalves, M. A., et al., *Efficient generation and amplification of high-capacity adeno-associated virus/adenovirus hybrid vectors*. J Virol, 2002. 76(21): p. 10734-44.
25. Epstein, A. L. and R. Manservigi, *Herpesvirus/retrovirus chimeric vectors*. Curr Gene Ther, 2004. 4(4): p. 409-16.
26. Ledinko, N. and H. W. Toolan, *Human adenovirus type 12 as a "helper" for growth of H-1 virus*. J Virol, 1968. 2(2): p. 155-6.
27. Fox, E., P. T. Moen, Jr., and J. W. Bodnar, *Replication of minute virus of mice DNA in adenovirus-infected or adenovirus-transformed cells*. Virology, 1990. 176(2): p. 403-12.
28. El-Andaloussi, N., et al., *Novel adenovirus based helper system to support production of recombinant parvovirus*. Cancer Gene Therapy, 2011. 18, 240-249.
29. Hillen, W. and C. Berens, *Mechanisms underlying expression of Tn10 encoded tetracycline resistance*. Annu Rev Microbiol, 1994. 48: p. 345-69.
30. Yao, F., et al., *Tetracycline repressor, tetR, rather than the tetR-mammalian cell transcription factor fusion derivatives, regulates inducible gene expression in mammalian cells*. Hum Gene Ther, 1998. 9(13): p. 1939-50.
31. Kestler, J., et al., *cis requirements for the efficient production of recombinant DNA vectors based on autonomous parvoviruses*. Hum Gene Ther, 1999. 10(10): p. 1619-32.
32. Lagrange, M., et al., *Intracellular scFvs against the viral E6 oncoprotein provoke apoptosis in human papilloma-

*virus-positive cancer cells.* Biochem Biophys Res Commun, 2007. 361(2): p. 487-92.
33. Chartier, C., et al., *Efficient generation of recombinant adenovirus vectors by homologous recombination in Escherichia coli.* J Virol, 1996. 70(7): p. 4805-10.
34. Bodendorf, U., et al., *Nuclear export factor CRM1 interacts with nonstructural proteins NS2 from parvovirus minute virus of mice.* J Virol, 1999. 73(9): p. 7769-79.
35. Mittereder, N., K. L. March, and B. C. Trapnell, *Evaluation of the concentration and bioactivity of adenovirus vectors for gene therapy.* J Virol, 1996. 70(11): p. 7498-509.
37. Raykov et al., Gene Therapy, Vol. 9, No. 5, 2002, pp. 358-362.
38. WO 03/061582 A2

The invention is further described by the following numbered paragraphs:

1. A chimeric adeno-parvovirus vector characterized in that it comprises the entire parvovirus genome inserted into an adenovirus genome, wherein:
   (a) the adenovirus genome is characterized by deletion of E1 and E3; and
   (b) the activity of at least the parvoviral protein NS is repressed or blocked in the packaging cell line during chimera production but is fully functional in cancer cells.
2. The chimeric adeno-parvovirus vector of paragraph 1, wherein the expression of NS is reduced or eliminated.
3. The chimeric adeno-parvovirus vector of paragraph 1 or 2, wherein the NS protein is NS1.
4. The chimeric adeno-parvovirus vector of paragraph 2 or 3, wherein the parvoviral P4 early promoter directing the NS expression is modified.
5. The chimeric adeno-parvovirus vector of paragraph 4, wherein the parvoviral P4 early promoter directing the NS expression is modified such that expression can be blocked by a tetracycline repressor.
6. The chimeric adeno-parvovirus vector of any one of paragraphs 1 to 5, wherein the adenovirus is Ad5.
7. The chimeric adeno-parvovirus vector of any one of paragraphs 1 to 6, wherein the parvovirus is a rodent parvovirus.
8. The chimeric adeno-parvovirus vector of paragraph 7, wherein the rodent parvovirus is LuIII, Mouse minute virus (MMV), Mouse parvovirus (MPV), Rat minute virus (RMV), Rat parvovirus (RPV), Rat virus (RV) or H1 (H1-PV).
9. The chimeric adeno-parvovirus vector of any one of paragraphs 1 to 8 additionally containing an expressible transgene.
10. The chimeric adeno-parvovirus vector of paragraph 9, wherein expression of the transgene is under the control of the P38 promoter.
11. The chimeric adeno-parvovirus vector of paragraph 9 or 10, wherein the transgene is a gene encoding a marker protein.
12. The chimeric adeno-parvovirus vector of paragraph 9 or 10, wherein the transgene is a gene encoding a therapeutic or immunogenic polypeptide.
13. The chimeric adeno-parvovirus vector of paragraph 12, wherein the transgene is a gene encoding a cytotoxic polypeptide, cytokine, chemokine, a cancer-specific peptide, ligand, adaptor, affibody, single chain antibody and/or a polypeptide enhancing PV oncolysis and/or PV replication.
14. A method of preparing a chimeric adeno-parvovirus vector characterized in that
   (i) mammalian cells are transfected with a chimeric adeno-parvovirus vector according to any one of paragraphs 1 to 13 and cultured under conditions blocking the expression of the parvoviral NS transcription unit; and
   (ii) the chimeric adeno-parvovirus is isolated from the mammalian cells or the medium after culturing the cells.
15. The method of paragraph 14, wherein the mammalian cells are HEK 293 cells.
16. The method of paragraph 15, wherein the mammalian cells are HEK T-REx™-293 cells and the vector is propagated in the presence of doxycycline (dox).
17. Chimeric adeno-parvovirus vector obtainable by a method of any one of paragraphs 14 to 16.
18. Cell containing the chimeric adeno-parvovirus vector of any one of paragraphs 1 to 13 or the vector obtained by a method according to any one of paragraphs 14 to 16.
19. Pharmaceutical composition containing the chimeric adeno-parvovirus vector of any one of paragraphs 1 to 13 or the vector obtained by a method according to any one of paragraphs 14 to 16 and a pharmaceutically acceptable carrier.
20. Chimeric adeno-parvovirus vector of any one of paragraphs 1 to 13 or the vector obtained by a method according to any one of paragraphs 14 to 16 for use in treating a tumor.
21. Chimeric adeno-parvovirus vector of any one of paragraphs 1 to 13 or the vector obtained by a method according to any one of paragraphs 14 to 16 for the use according to paragraph 20 characterized in that the use is for treating a PV resistant tumor.
22. Chimeric adeno-parvovirus vector of any one of paragraphs 1 to 13 or the vector obtained by a method according to any one of paragraphs 14 to 16 for the use according to paragraph 20 or 21 characterized in that the use is for treating cervical carcinomas, melanomas, lung and colon cancers.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A chimeric adeno-parvovirus vector characterized in that it comprises an entire parvovirus genome inserted into an adenovirus genome, wherein:
    (a) The adenovirus genome is characterized by deletion of E1 and E3; and
    (b) the activity of a parvovirus P4 early promoter, which regulates the expression of a nonstructural parvovirus protein (NS) is modified to repress or block the NS protein expression in a packaging cell line during chimera production but is fully functional in cancer cells with respect to the activity of a wild-type parvovirus P4 early promoter,
    wherein the parvovirus P4 early promoter is modified by inserting two tetracycline operator 2 elements between a TATA box and a NS start codon.

2. The chimeric adeno-parvovirus vector of claim 1, wherein the expression of NS is reduced or eliminated.

3. The chimeric adeno-parvovirus vector of claim 1, wherein the NS protein is NS1 and/or NS2.

4. The chimeric adeno-parvovirus vector of claim 1, wherein the adenovirus is Ad5.

5. The chimeric adeno-parvovirus vector of claim 1, wherein the parvovirus is a rodent parvovirus.

6. The chimeric adeno-parvovirus vector of claim 5, wherein the rodent parvovirus is LuIII, Mouse minute virus (MMV), Mouse parvovirus (MPV), Rat minute virus (RMV), Rat parvovirus (RPV), Rat virus (RV) or H1 parvovirus (H1-PV).

7. The chimeric adeno-parvovirus vector of claim 1 additionally containing an expressible transgene.

8. The chimeric adeno-parvovirus vector of claim 7, wherein expression of the transgene is under the control of the parvovirus P38 promoter.

9. The chimeric adeno-parvovirus vector of claim 7, wherein the transgene is a gene encoding a marker protein.

10. The chimeric adeno-parvovirus vector of claim 7, wherein the transgene is a gene encoding a therapeutic or immunogenic polypeptide.

11. The chimeric adeno-parvovirus vector of claim 10, wherein the transgene is a gene encoding a cytotoxic polypeptide, cytokine, chemokine, a cancer-specific peptide, ligand, adaptor, affibody and/or single chain antibody.

12. A cell containing the chimeric adeno-parvovirus vector of claim 1.

13. A pharmaceutical composition containing the chimeric adeno-parvovirus vector of claim 1, and a pharmaceutically acceptable carrier.

14. A method of preparing a chimeric adeno-parvovirus vector, the method comprising:
    (i) mammalian cells are transfected with a chimeric adeno-parvovirus vector according to claim 1 and cultured under conditions blocking the expression of the parvovirus NS transcription unit; and
    (ii) the chimeric adeno-parvovirus is isolated from the mammalian cells or the medium after culturing the cells.

15. The method of claim 14, wherein the mammalian cells are HEK 293 cells.

16. The method of claim 15, wherein the mammalian cells are HEK-293 cells comprising a constitutively expressed tetracycline repressor protein and the vector is propagated in the presence of doxycycline (dox).

17. A method for treating an individual with a tumor in need of treatment therefor comprising administering the chimeric adeno-parvovirus vector of claim 1 to the individual.

18. The method of claim 17 wherein the tumor is a PV resistant tumor.

19. The method of claim 17 wherein the tumor is one or more of a cervical carcinoma, a melanoma, a lung cancer, and a colon cancer.

* * * * *

SEQUENCE LISTING

```
<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
```

```
<221> NAME/KEY: source
<222> LOCATION: 1..30
<223> OTHER INFORMATION: /mol_type="DNA"
      /note="PCR_primer"
      /organism=Artificial Sequence

<400> SEQUENCE: 1
aaactcgagg cggttcaggg agtttaaacc                                            30

<210> SEQ ID NO 2
<211> LENGTH: 75
<212> TYPE: DNA
<213> ORGANISM: Artificial Sequence
<220> FEATURE:
<221> NAME/KEY: source
<222> LOCATION: 1..75
<223> OTHER INFORMATION: /mol_type="DNA"
      /note="PCR-primer"
      /organism=Artificial Sequence

<400> SEQUENCE: 2
aactgacttc tctctatcac tgatagggag atctctatca ctgataggga agtagttgct          60
tatatacttt aaacc                                                           75

<210> SEQ ID NO 3
<211> LENGTH: 76
<212> TYPE: DNA
<213> ORGANISM: Artificial Sequence
<220> FEATURE:
<221> NAME/KEY: source
<222> LOCATION: 1..76
<223> OTHER INFORMATION: /mol_type="DNA"
      /note="PCR-primer"
      /organism=Artificial Sequence

<400> SEQUENCE: 3
agcaactact tccctatcag tgatagagat ctccctatca gtgatagaga gaagtcagtt          60
acttatcttt tctttc                                                          76

<210> SEQ ID NO 4
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
      /note="PCR-primer"
      /organism=Artificial Sequence

<400> SEQUENCE: 4
aaaaagcttc catccgatat cttttccatt cag                                       33

<210> SEQ ID NO 5
<211> LENGTH: 37
<212> TYPE: DNA
<213> ORGANISM: Artificial Sequence
<220> FEATURE:
<221> NAME/KEY: source
<222> LOCATION: 1..37
<223> OTHER INFORMATION: /mol_type="DNA"
      /note="annealed oligonucleotides"
      /organism=Artificial Sequence

<400> SEQUENCE: 5
gttcatagcc catatatgga gttcagatct ggtaccg                                   37
```

```
<210> SEQ ID NO 6
<211> LENGTH: 37
<212> TYPE: DNA
<213> ORGANISM: Artificial Sequence
<220> FEATURE:
<221> NAME/KEY: source
<222> LOCATION: 1..37
<223> OTHER INFORMATION: /mol_type="DNA"
      /note="annealed oligonucleotides"
      /organism=Artificial Sequence

<400> SEQUENCE: 6
cggtaccaga tctgaactcc atatatgggc tatgaac                              37

<210> SEQ ID NO 7
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="DNA"
      /note="PCR-Primer"
      /organism=Artificial Sequence

<400> SEQUENCE: 7
aaggaaaaaa gtcgactttt gtgatgctcg tca                                  33

<210> SEQ ID NO 8
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="DNA"
      /note="PCR-Primer"
      /organism=Artificial Sequence

<400> SEQUENCE: 8
aggaaaaaag atatcttttc cattcagttg a                                    31

<210> SEQ ID NO 9
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="DNA"
      /note="annealed oligonucleotide"
      /organism=Artificial Sequence

<400> SEQUENCE: 9
taatagtgag aattctcact atta                                            24

<210> SEQ ID NO 10
<211> LENGTH: 330
<212> TYPE: DNA
<213> ORGANISM: Artificial Sequence
<220> FEATURE:
<221> NAME/KEY: source
<222> LOCATION: 1..330
<223> OTHER INFORMATION: /mol_type="DNA"
      /note="P4-TO promoter"
      /organism=Artificial Sequence

<400> SEQUENCE: 10
aaactccctg aaccgcttat cattttttaga actgaccaac catgttcacg taagtgacgt    60
```

```
gatgacgcgc gctgcgcgcg cgccttcggc agtcacacgt cacttacgtt tcacatggtt    120
ggtcagttct aaaaatgata agcggttcag ggagtttaaa ccaaggcgcg aaaaggaagt    180
gggcgtggtt taaagtatat aagcaactac ttccctatca gtgatagaga tctccctatc    240
agtgatagag agaagtcagt tacttatctt ttctttcatt ctgtgagtcg agacgcacag    300
aaagagagta accaactaac catggctgga                                     330
```